(12) United States Patent
Henriksen et al.

(10) Patent No.: US 9,895,088 B2
(45) Date of Patent: Feb. 20, 2018

(54) HEARING PROTECTION DEVICE WITH INTEGRATED AUDIOMETRIC TESTING

(71) Applicant: HONEYWELL HEARING TECHNOLOGIES AS, Trondheim (NO)

(72) Inventors: Viggo Henriksen, Trondheim (NO); Trym Holter, Trondheim (NO); Olav Kvaloy, Hundhamarem (NO); Asle Melvaer, Bekkestua (NO); Georg Esa Ottesen, Trondheim (NO); Odd Kristen Ostern Pettersen, Trondheim (NO); Jarle Svean, Trondheim (NO); Svein Sorsdal, Trondheim (NO)

(73) Assignee: Honeywell Hearing Technologies AS, Trondheim (NO)

( * ) Notice: Subject to any disclaimer, the term of this patent is extended or adjusted under 35 U.S.C. 154(b) by 0 days.

(21) Appl. No.: 15/263,907

(22) Filed: Sep. 13, 2016

(65) Prior Publication Data

US 2016/0374595 A1    Dec. 29, 2016

Related U.S. Application Data

(63) Continuation of application No. 13/192,275, filed on Jul. 27, 2011, now Pat. No. 9,554,733.
(Continued)

(51) Int. Cl.
*A61B 5/00* (2006.01)
*A61B 5/12* (2006.01)
(Continued)

(52) U.S. Cl.
CPC .............. *A61B 5/12* (2013.01); *A61B 5/121* (2013.01); *A61B 5/123* (2013.01); *A61F 11/08* (2013.01);
(Continued)

(58) Field of Classification Search
CPC ............ A61B 5/121; A61B 5/12; H04R 25/70
(Continued)

(56) References Cited

U.S. PATENT DOCUMENTS

| 4,038,496 A | 7/1977 | Feezor |
| 5,197,332 A | 3/1993 | Shennib |

(Continued)

FOREIGN PATENT DOCUMENTS

| WO | 03030619 A2 | 4/2003 |
| WO | 2008139404 A1 | 11/2008 |
| WO | 2012014175 A1 | 2/2012 |

OTHER PUBLICATIONS

PCT/IB2011/053371, International Search Report dated Dec. 20, 2011, 5 pages.
(Continued)

*Primary Examiner* — Daniel Cerioni
(74) *Attorney, Agent, or Firm* — Conley Rose, P.C.

(57) ABSTRACT

A hearing protection device is disclosed which incorporates integrated audiometric testing, thereby allowing for testing without removal of safety hearing protection. The hearing protection is typically intended to be worn for the duration of a work shift, and allows for self-testing during the shift. Embodiments of the device may utilize a series of partial test sessions, so that each test session is kept brief so as to not interfere unduly with the work schedule. This may encourage frequent testing, hopefully aiding in early detection of potential hearing loss. Additionally, methods of use are disclosed.

20 Claims, 10 Drawing Sheets

Related U.S. Application Data

(60) Provisional application No. 61/368,446, filed on Jul. 28, 2010.

(51) Int. Cl.
  *A61F 11/08* (2006.01)
  *A61F 11/14* (2006.01)
  *H04R 1/10* (2006.01)

(52) U.S. Cl.
  CPC ...... *H04R 1/1083* (2013.01); *A61F 2011/145* (2013.01); *H04R 1/1091* (2013.01)

(58) Field of Classification Search
  USPC .......................................... 600/559
  See application file for complete search history.

(56) References Cited

U.S. PATENT DOCUMENTS

| | | |
|---|---|---|
| 5,333,622 A | 8/1994 | Casali et al. |
| 5,970,795 A | 10/1999 | Seidmann et al. |
| 6,118,877 A | 9/2000 | Lindemann et al. |
| 6,350,243 B1 | 2/2002 | Johnson |
| 6,396,930 B1 | 5/2002 | Vaudrey et al. |
| 6,456,199 B1 | 9/2002 | Michael |
| 6,567,524 B1 | 5/2003 | Svean et al. |
| 6,661,901 B1 | 12/2003 | Svean et al. |
| 6,754,359 B1 | 6/2004 | Svean et al. |
| 7,037,274 B2 | 5/2006 | Thornton et al. |
| 7,039,195 B1 | 5/2006 | Svean et al. |
| 7,132,949 B2 | 11/2006 | Harrison et al. |
| 7,288,072 B2 | 10/2007 | Stott et al. |
| 7,465,277 B2 | 12/2008 | Wasden et al. |
| 7,574,917 B2 | 8/2009 | Von Dach et al. |
| 9,554,733 B2 | 1/2017 | Henriksen et al. |
| 2003/0083591 A1* | 5/2003 | Edwards ............... A61B 5/121 600/559 |
| 2004/0006283 A1 | 1/2004 | Harrison et al. |
| 2004/0039299 A1 | 2/2004 | Harrison et al. |
| 2004/0071295 A1 | 4/2004 | Wasden et al. |
| 2004/0073136 A1 | 4/2004 | Thornton et al. |
| 2005/0033193 A1 | 2/2005 | Wasden et al. |
| 2007/0129649 A1 | 6/2007 | Thornton et al. |
| 2007/0204694 A1 | 9/2007 | Davis |
| 2007/0223720 A1 | 9/2007 | Goldberg et al. |
| 2007/0223721 A1 | 9/2007 | Stern et al. |
| 2008/0011084 A1 | 1/2008 | Von Dach et al. |
| 2008/0013744 A1 | 1/2008 | Von Dach et al. |
| 2008/0130906 A1 | 6/2008 | Goldstein et al. |
| 2008/0144841 A1 | 6/2008 | Goldstein et al. |
| 2008/0144842 A1 | 6/2008 | Goldstein et al. |
| 2008/0219486 A1 | 9/2008 | Goldstein et al. |
| 2009/0156959 A1 | 6/2009 | Thornton et al. |
| 2009/0190786 A1 | 7/2009 | Miskiel et al. |
| 2010/0135502 A1 | 6/2010 | Keady et al. |

OTHER PUBLICATIONS

Levitt, H.; "Transformed Up-Down Methods in Psychoacoustics", Journal of the Acoustical Society of America, vol. 49, Issue 2B, Abstract, http://asadl.org/jasa/resource/1/jasman/v49/i2B/p467_s1?isAuthorized=no, Feb. 23, 2012, 1 page.
PCT/IB2011/053371, International Preliminary Report on Patentability, dated Jan. 29, 2013, 7 pages.
PCT/IB2011/053371, Written Opinion of the International Searching Authority, dated Dec. 20, 2011, 6 pages.
U.S. Appl. No. 13/192,275, Office Action, dated Apr. 10, 2013, 16 pages.
U.S. Appl. No. 13/192,275, Final Office Action, dated May 30, 2013, 16 pages.
U.S. Appl. No. 13/192,275, Advisory Action, dated Jul. 23, 2013, 3 pages.
U.S. Appl. No. 13/192,275, Notice of Panel Decision from Pre-Appeal Brief Review, dated Aug. 19, 2013, 2 pages.
U.S. Appl. No. 13/192,275, Examiner's Answer to Appeal Brief, dated Nov. 7, 2013, 35 pages.
U.S. Appl. No. 13/192,275, Decision on Appeal, dated May 25, 2016, 15 pages.
U.S. Appl. No. 13/192,275, Miscellaneous Action, dated Jul. 14, 2016, 2 pages.
U.S. Appl. No. 13/192,275, Notice of Allowance, dated Sep. 29, 2016, 7 pages.
Europe Patent Application No. 11763768.6, Office Action, dated Mar. 7, 2013, 2 pages.
Europe Patent Application No. 11763768.6, Office Action, dated Apr. 7, 2017, 6 pages.
Australia Patent Application No. 2011284283, Office Action, dated Aug. 13, 2013, 4 pages.
Australia Patent Application No. 2011284283, Office Action, dated Sep. 1, 2014, 5 pages.
Australia Patent Application No. 2011284283, Notice of Acceptance, dated Oct. 27, 2014, 2 pages.

* cited by examiner

The two-way digital interface may be wired, wireless (RF) or optical (IR).

HEARING PROTECTION DEVICE WITH INTEGRATED AUDIOMETRIC TESTING

CROSS-REFERENCE TO RELATED APPLICATIONS

This application is a continuation of and claims priority benefit under 35 U.S.C. § 120 to co-pending U.S. patent application Ser. No. 13/192,275, filed on Jul. 27, 2011, and entitled "HEARING PROTECTION DEVICE WITH INTEGRATED AUDIOMETRIC TESTING", which is related as a non-provisional of and claims benefit under 35 U.S.C. § 119 to U.S. Provisional Patent Application Ser. No. 61/368,446 entitled "HEARING PROTECTION DEVICE WITH INTEGRATED AUDIOMETRIC TESTING" and filed Jul. 28, 2010 (such that the present application claims priority to both earlier applications and thereby claims an effective filing date of Jul. 28, 2010 due to priority), both of which are hereby incorporated by reference for all purposes as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

FIELD

Disclosed embodiments relate generally to improved hearing protection, and more specifically to safety hearing protection devices to be worn in loud, potentially damaging environments and that serve to both protect the user's hearing from damage and to test the user's hearing to determine hearing threshold and/or to allow for an initial, assessment to detect potential hearing loss.

BACKGROUND

In many industrial settings, workers are routinely exposed to potentially damaging noise environments during their workday. The issue of potential hearing damage often arises in manufacturing and other industrial facilities, but may also arise in military settings, airport settings, and other work environments that involve potentially damaging noise exposure. There is a need to both protect against hearing damage and also to monitor workers' hearing to determine if there has been any significant hearing loss due to environmental noise. Hearing protection and hearing monitoring may work synergistically together to provide improved hearing protection, since the ability to monitor for hearing loss allows for better evaluation of the effectiveness of the hearing protection and allows for corrective action to be taken at an early stage (which may limit permanent hearing loss, possibly by allowing action at the first signs of temporary hearing loss). Examples of corrective action could include modifying and/or supplementing hearing protection, reducing time in the noise environment, and/or removing the worker from the noise environment, by way of non-exclusive example.

To be effective for this purpose, embodiments of the present invention may offer both hearing protection and hearing testing, and may provide regular hearing testing in a way that is not burdensome or time or labor intensive. Rather, it offers a convenient approach that may easily be integrated into the standard workday without any significant disruption to routine. Providing an integrated hearing test within safety hearing protection that workers will wear anyway (for example, for OSHA compliance) may also allow for self-administered audiometric testing that may be run independent of location. The convenience of this type of integrated design makes regular, frequent audiometric testing easier to perform, and by increasing the frequency of such testing, may ultimately result in improved hearing protection.

SUMMARY

In one aspect, the disclosure includes a device which may comprise: a sealing section or hearing protection device (for providing sound attenuation to protect a user's ears from potentially damaging external sounds); a sound generation means (such as a speaker) operable to and capable of producing sound stimuli at various frequencies and sound pressure levels; and an electronics unit configured to be operable to and capable of generating one or more test signals directed to the sound generator means in order to cause generation of sound stimuli for an audiometric test, and typically having a user interface (for controlling the test and receiving user responses), a memory for storing responses and/or test results, and optionally an interface for uploading test results to an external computer system. In an embodiment, the electronics unit may be configured/programmed to be operable to administer an audiometric test by implementing a test protocol/procedure, and the electronics unit may optionally include a memory for storing the test protocol. Rather than test the entire range of hearing to produce a full audiometric profile, the test protocol of an embodiment may be directed towards a partial profile, which only tests a smaller subset of specific frequencies. By way of example, the partial profile may test frequencies in a range from 3-6 kHz, and in an embodiment, may for example test only 3 kHz, 4 kHz, and 6 kHz (in an attempt to provide an initial, quick assessment or screening of potential hearing damage). Additionally, in an embodiment, the partial profile may be tested over a series of partial test sessions, with each test session testing only a portion of the frequencies included in the profile. In an embodiment, the partial test session would tend to be short, typically allowing for completion of the test session in less than about 30 seconds (thereby allowing for frequent testing without unduly interfering with other activities, such as work schedule). In one embodiment, each test session might test only one ear for a single frequency. If hearing loss is detected by the audiometric test, the device may warn the user, indicating a threshold shift. By way of example, the electronics unit could transmit a signal to the sound generation means to generate an audible warning. Alternatively, the electronics unit might include a warning light or other warning mechanism to notify the user if hearing loss is detected.

In an embodiment, testing each ear for a specific frequency would be an iterative process that hones-in on the user's hearing threshold (based on a plurality of test sound stimuli responses). For each frequency, a series of test sound stimuli would be generated by the sound generator means at varying sound pressure levels. The user would respond (by activating the user interface, for example) to register a positive response (indicating that the sound was heard), or if the user does not respond within a pre-set timeframe (typically between 1 and 5 seconds) the electronics unit would register a negative response (indicating that the user is unable to hear that frequency at that sound pressure level). Typically, the iterative series of sound stimuli would be altered based on the user's responses. In one embodiment, the user's hearing threshold might be determined using a statistical model (such as the psychometric function) describing the probability for a positive user response as a function of the stimulus level. The psychometric function tends to have a sigmoid characteristic, shaped such that it approaches 0 (or perhaps a value higher than zero, if false positives are considered) for very low stimulus levels and 1 for very high stimulus levels. In relation to this function, the hearing threshold would typically be defined as the stimulus level that corresponds to 50% probability of a positive user response. In an embodiment, the psychometric function has a pre-set shape, but its displacement along the x-axis (the stimulus level axis) may be unknown prior to the audiometric test. In one embodiment, its displacement along the x-axis may be determined during the test based on the Maximum Likelihood principle, such that after any given number of stimulus-response pairs, the probability that the statistical model could have generated the observed data (stimulus-response pairs) is maximized. In one embodiment, the next stimulus level is selected such that it coincides with the present hearing threshold level estimate. For a positive response the next sound stimulus would typically then be below the previous sound stimulus level, and for a negative response the next sound stimulus would typically be above the previous sound stimulus level. It is an inherent property of such a statistical method that, with an increasing number of observed stimulus-response pairs, the deviation between succeeding stimulus levels will typically become smaller. The method therefore allows for honing-in on the hearing threshold with added precision. In one embodiment, the initial sound stimulus might be set at a fairly high sound pressure level (which might be a pre-set number, or might be based on the user's assumed hearing threshold based on pre-existing information) in order to get the user's attention (although optionally, the initial sound stimulus could be set at any sound pressure level, and could alternatively proceed upward from a low sound pressure level, for example). The iterative series of tests (i.e. sound stimuli) would typically proceed until a stop condition occurs. In an embodiment, the stop condition may be a pre-set number of iterations (typically between 5 and 10). In another embodiment, the stop condition could be a difference between succeeding stimulus levels that is sufficiently small (such as less than 2 dB). In an embodiment, each test session would test only a single ear for a single frequency, and the electronics unit would cycle through a series of test sessions (each with a different frequency and/or ear) in order to test the entire range of the audiometric profile according to the test protocol. In other words, the profile would be generated by compiling the series of test sessions, and then the series might start again (to begin gathering data for the next profile in time).

Alternative (non-statistical) iterative testing procedures might also exist. For example, rather than utilizing a statistical model, embodiments of the test could generate an iterative series of sound stimuli that would be altered based on the user's responses using a pattern of incremental changes. For example, staircase methods or a Bekesy tracking method could be used to determine the user's hearing threshold. So for an exemplary embodiment using a staircase method, for a positive response the next sound stimulus would be set at an increment (step) below the previous sound stimulus level (ix, the next sound stimulus would be determined by subtracting an increment/step from the most recently used sound stimulus level the one that the response relates to), and for a negative response the next sound stimulus would be set at an increment (step) above the previous sound stimulus level (i.e. the next sound stimulus would be determined by adding an increment/step to the most recently used sound stimulus level—the one that the response relates to). In an embodiment, the incremental change in descending runs (caused by positive responses to stimuli) might be twice that of the incremental change in ascending runs (caused by negative responses to stimuli). So in one embodiment, for example, the steps in descending runs might be 10 dB, while the steps in ascending runs might be 5 dB. In one embodiment, the initial sound stimulus might be set at a fairly high sound pressure level (which might be a pre-set number, or might be based on the user's assumed hearing threshold based on pre-existing information) in order to get the user's attention (although optionally, the initial sound stimulus could be set at any sound pressure level, and could proceed upward from a low sound pressure level, for example). The iterative series of tests (i.e. sound stimuli) would typically proceed until a stop condition occurs. In an embodiment, the stop condition may be a pre-set number of iterations (typically between 5 and 10). In another embodiment, the stop condition could be that a pre-set number of turning points (typically six to eight) between runs has been reached. In an embodiment, each test session would test only a single ear for a single frequency, and the electronics unit would cycle through a series of test sessions (each with a different frequency or ear) in order to test the entire range of the audiometric profile according to the test protocol. In other words, the profile would be generated by compiling the series of test sessions, and then the series might start again (to begin gathering data for the next profile in time).

In another embodiment, the device might further comprise a microphone for detecting sound levels in the ear canal (near the eardrum) under the sealing element. This would allow for noise exposure levels to be determined and recorded. In an embodiment, the electronics unit could then warn the user of exposure to potentially damaging noise levels (despite the hearing protection offered by the device), allowing the user to initiate a test to check for any hearing damage. Alternatively, the electronics unit could automatically administer a test based on the warning. Indeed, in some embodiments the electronics unit could select specific frequencies to test based on detected noise exposure levels. In another embodiment, the noise level could be used to determine whether conditions are adequate for audiometric testing, or whether the background noise levels are too high for accurate testing. The electronics unit might warn the user of excessive background noise, or alternatively could prevent initiation of a test session until the background noise is reduced to acceptable levels.

In another aspect, the disclosure includes a method of preliminarily screening for hearing loss in the workplace (without removing hearing protection being worn to protect against noise exposure in the workplace, using a hearing protection device with integrated audiometric testing) without unduly interfering with work schedule, comprising the steps of: sealing the user's ear canal (by applying a hearing protection device to protect the user from potentially damaging external noise) while the user is in an environment with potential noise exposure (such that the sealing lasts substantially as long as the potential for external noise exposure, for example the duration of a shift); activating an audiometric test without removing the hearing protection device; and determining an estimated hearing threshold based on the audiometric test, wherein the hearing protection is worn by the user for a period of time that is greater than the duration of the audiometric test session. In an embodiment, the audiometric test is a partial profile (testing only a portion of the audiometric profile to be determined according to the test protocol), and a series of partial test sessions are run (typically with only one session per shift or day, each testing only a portion of the profile) and compiled over time to determine the user's estimated audiometric profile (which may be a partial profile). In an embodiment, the hearing protection device is worn by the user for the duration of exposure to an environment of potential noise (such that the duration of hearing protection is significantly longer than the duration of the audiometric test session).

In another embodiment, the noise level is measured and/or recorded. Optionally, the measured noise level may then be used to determine if conditions are appropriate for an audiometric test (i.e. checking to ensure that the background noise level is not too high for effective testing). The measured noise level might also be used to initiate an audiometric test (if the noise level was sufficiently high to indicate possible hearing damage). This measure noise level might also be used to select specific frequencies to test. In yet another embodiment, the quality of the seal provided by the hearing protection device is checked. In another embodiment, the audiometric test comprises generation of a series of sound stimuli, registering/recording user responses, and analyzing the responses to determine an estimated hearing threshold. In an embodiment, the series of sound stimuli are iteratively adjusted based on the user responses to hone-in on the hearing threshold. In yet another embodiment, additional sound attenuation (such as active noise reduction and/or passive noise reduction earmuffs over an earplug-type hearing protection device) be used and/or the user may change locations (to a location with less background noise) to provide conditions favorable to testing.

Another embodiment might include pre-testing of the user's hearing (typically using a detailed audiometric test performed by trained audiologists) to provide a benchmark for analysis of hearing damage. In another embodiment, the test results (such as estimated hearing threshold) would be uploaded to an external computer, allowing for analysis of potential hearing loss (by looking for changes to the hearing threshold over time, typically by comparing the current estimated hearing threshold to previous results). If this preliminary screening indicates possible hearing damage, then in an embodiment the user might undergo more thorough audiometric testing. In another embodiment, the user might be warned.

In another aspect, the disclosure includes a method for protecting a user's hearing during a work shift and performing a quick screening for potential hearing loss without unduly interfering with work using a hearing protection device with integrated audiometric testing, comprising: employing the hearing protection device (during the duration of the work shift to protect the user from a potentially damaging noise environment); transmitting a series of sound stimuli into the user's ear canal (via a speaker in the hearing protection device) while the hearing protection device is employed (and the user's ear canal is sealed); registering/recording user responses to each of the sound stimuli (via an electronics unit with an interface), and analyzing the user responses to determine an estimated hearing threshold, wherein the hearing protection device is employed for a duration that substantially exceeds the series of sound stimuli. In an embodiment, the series of sound stimuli are incrementally adjusted based on user responses in order to hone-in on the hearing threshold. In another embodiment, the series of sound stimuli are each separated by a pause; and the duration of the pause is a standardized minimum following a negative user response, but the duration of the pause includes a randomized amount or segment, typically between about 0-3 seconds, in addition to the standardized minimum amount following a positive user response (such that the pause following a positive user response is a randomized amount that is equal to or greater than the standardized minimum, often between about 2 and about 5 seconds in overall duration for example).

BRIEF DESCRIPTION OF THE DRAWINGS

For a more complete understanding of the present disclosure, and for further details and advantages thereof, reference is now made to the accompanying drawings, in which.

DETAILED DESCRIPTION

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or has a characteristic, that particular component or feature is not required to be included or to have the characteristic.

Disclosed embodiments comprise a hearing protection device with an audiometric testing apparatus. Any sort of hearing protection device could be employed with the disclosed embodiments. By way of example, the hearing protection device could be an earplug, an ear muff, or any other means of sealing a user's ear to prevent sound from reaching the eardrum. Additionally, the type of hearing protection employed could be active (such as active noise cancelation), passive (such as sound attenuating materials), or some combination of the two techniques, by way of example. And the audiometric testing apparatus typically might include a sound generator (such as a speaker, for example, typically capable of generating sounds over at least a portion of the frequency range of human hearing) for projecting sound stimulus into the user's ear canal at various frequencies, an electronics unit that runs the audiometric test (generating one or more signals to the sound generator to implement the test and/or storing test results), and a user interface (that allows the user to interact with the electronics unit during the audiometric test). Typically, some or all of the elements of the audiometric testing apparatus would be housed within the hearing protection device, providing an integrated unit that allows for audiometric testing while the hearing protection device is in place protecting the user from potentially harmful external noise exposure.

Figure 1:
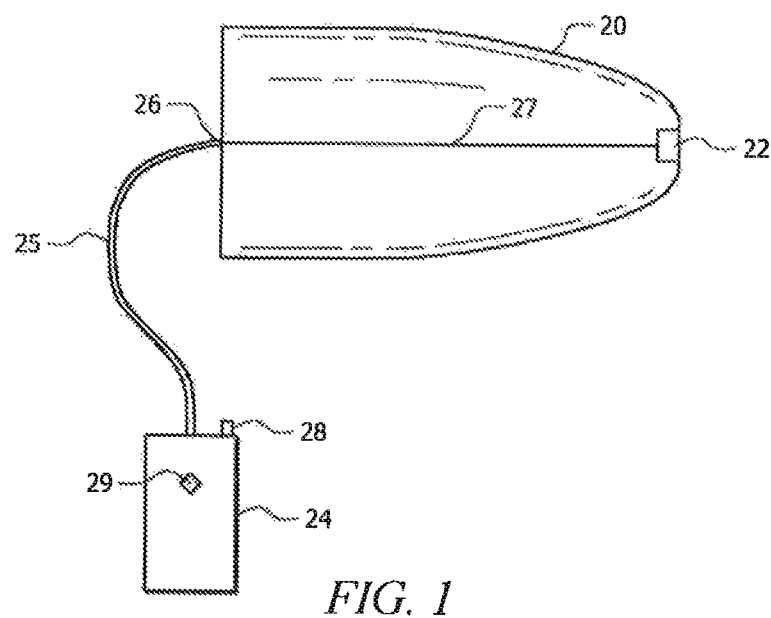
FIG. 1 is a sectional view of an embodiment of an earplug hearing protection device (HPD) with integrated audiometric testing, having an external electronics unit.
Figure 2:
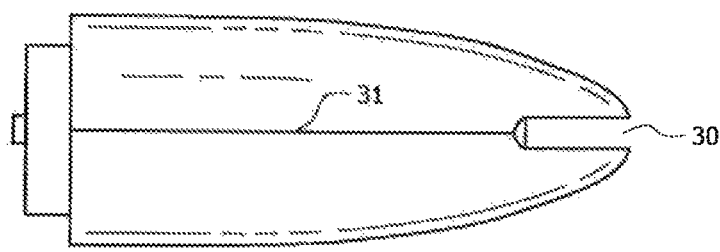
FIG. 2 is a sectional view of an embodiment of an all-in-ear earplug HPD.
Figure 3:
FIG. 3 is a sectional view of another embodiment of an all-in-ear earplug HPD.
Figure 4:
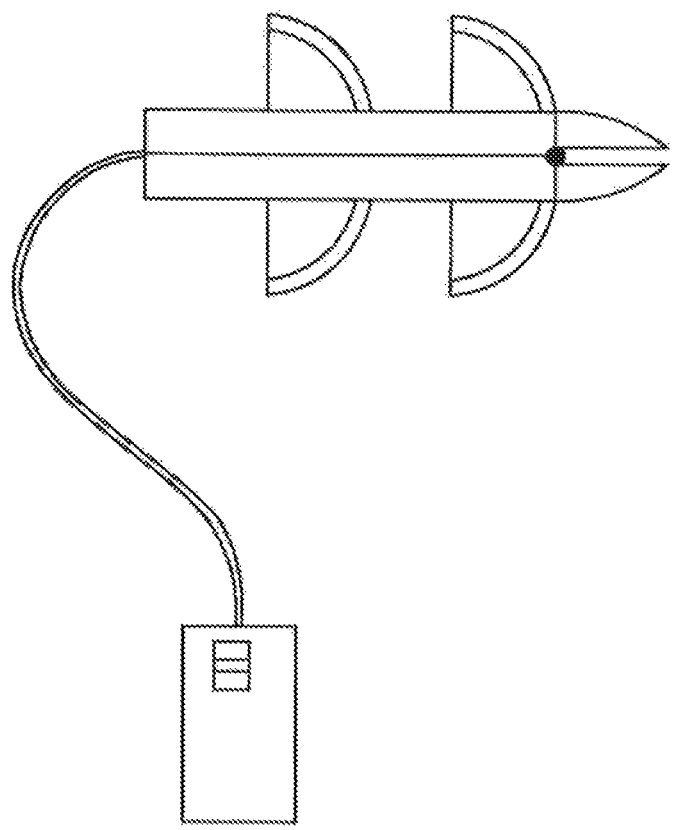
FIG. 4 is a sectional view of an embodiment of a flanged earplug HPD with external electronics unit.
Figure 5:
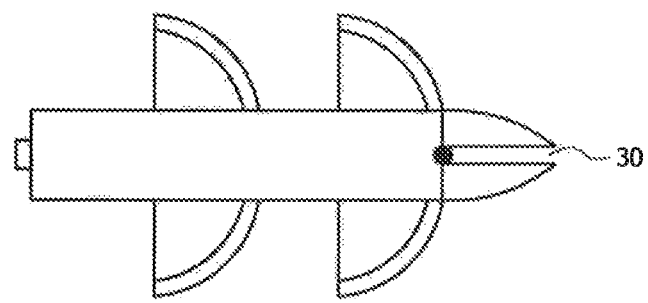
FIG. 5 is a sectional view of an embodiment of an all-in-ear flanged earplug HPD.
Figure 6:
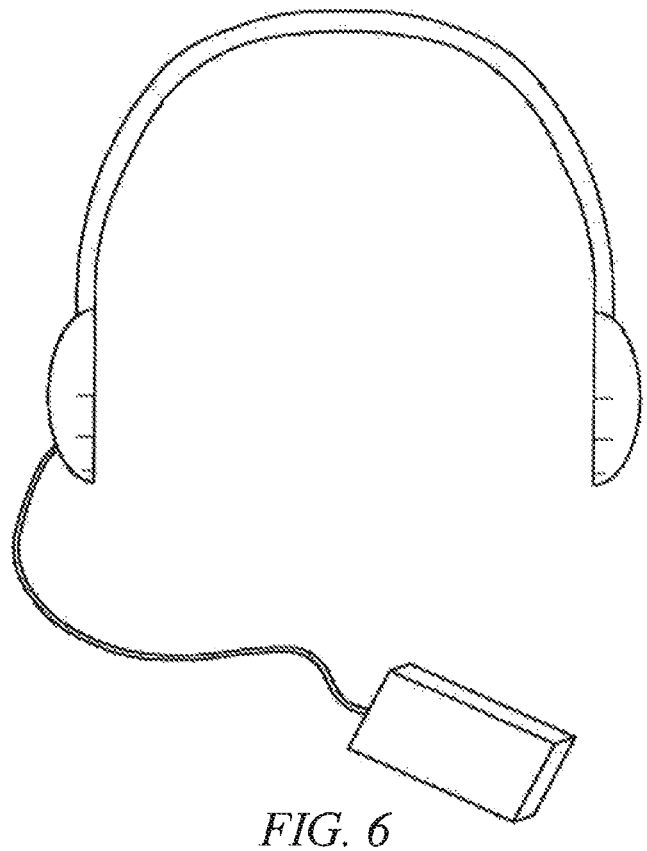
FIG. 6 is a view of an embodiment of an earmuff HPD with external electronics unit.

FIGS. 1-6 show several different embodiments of hearing protection devices with integrated audiometric testing. As the examples in these figures show, there are a variety of variants of the inventive concepts. FIGS. 1-2, for example, illustrate embodiments having a roll-down type earplug as the hearing protection device, while FIGS. 4-5 illustrate embodiments having a flanged-type earplug hearing protection device (typically providing press-in insertion). FIG. 6 does not use earplugs at all, but rather has an earmuff hearing protection device. Also, FIGS. 1, 4, and 6, for example, have an electronics unit that is external to the hearing protection device (with the user interface integrated into the electronics unit and with the sound generator located within the hearing protection device). In FIG. 1, the user interface is a button located on the electronics unit (although alternatively the user interface could be a microphone as shown in FIG. 4 to allow for voice activation, a separate user interface unit that communicates with the electronics unit, or any other sort of interface configuration). While these figures show a wire connection between the electronics unit and the sound generator in the hearing protection device, the interface could alternatively be wireless (such as RF), optical (such as IR), or any other means of electronic communication. FIGS. 2, 3, and 5, on the other hand, provide examples in which the audiometric testing apparatus is substantially contained within the hearing protection device (to provide an integrated in-ear device). And some embodiments, such as FIGS. 2-5, have a sound tube or channel through the earplug, allowing the sound generator access to the user's meatus when the earplug is in place in the user's ear (so that the sound generator may generate a sound field in the user's ear canal/meatus). And depending on the location of the sound generator (within the hearing protection device and with respect to the electronics unit of the audiometric testing apparatus), there may be a wire and/or cable connecting the sound generator to the electronics unit and/or running through a portion of the length of the earplug. The device could be an earplug-based hearing protection device with electronics in a separate unit, an earplug-based hearing protection device with miniaturized electronics in the earplug or at the ear, an earplug-based hearing protection device with electronics located behind the ear, an over-the-ear (earmuff) hearing protection device with built-in electronics, or an over-the-ear hearing protection device with electronics in a separate unit, by way of non-exclusive example. So it should be apparent from this disclosure that the present inventive concepts may be implemented in a variety of ways that include a hearing protection device and an audiometric testing apparatus.

The audiometric testing apparatus may be designed to test the hearing of the user, thereby determining the user's hearing threshold. Typically, the electronics unit would comprise a computer processor programmed/configured to run one or more audiometric test protocols, generating appropriate signals to cause the sound generator to generate one or more sound stimulus in the user's meatus in accordance with the programmed test protocols. The audiometric test regimen could be a full test designed to generate a complete audiometric profile of the user (for example, testing a series of frequencies across the range of human hearing, such as 100 Hz to 8 kHz for example), or it could be a partial test profile of only a portion of the hearing range (such as 3-6 kHz, for example, which tends to be the range in which damage is most likely to occur from exposure to noisy environments). Indeed, a partial test profile could even be targeted towards the specific frequencies of concern at a particular worksite environment (such that the audiometric test could be customized for the specific noise environment at issue, possibly based on previously measured noise levels).

Also, each test session could be only a portion of the complete audiometric test protocol regimen (i.e. a portion of the audiometric profile being tested), with a different portion of the audiometric test regimen being run each test session so that over time a series of test sessions can generate an entire audiometric test profile (which may be a partial test of only designated frequency ranges or a full test across the complete frequency range of human hearing). In a preferred embodiment, the audiometric testing apparatus would implement a pattern of partial tests that, when collated over time (i.e. a series of test sessions), would result in an audiometric profile of the user within the range of likely damage (typically from 3-6 kHz). It is even possible that each test session could test only a single ear at a single frequency (such that again, an audiometric profile could be built up over a series of test sessions). In the preferred embodiment, each test session (implementing a partial test) would be brief (so that it could be convenient and would not unduly affect the workday), typically lasting no more than about 30 seconds. In this embodiment, the audiometric testing apparatus would test one or more frequencies in one or more ears of the user to determine the hearing threshold for the tested frequency each session, and would remember which frequencies to test in which ears in the succeeding sessions to allow for build-up of an audiometric profile for the test range.

In one specific embodiment, each test session might only test a single ear at a single frequency, and a series of test sessions could construct a partial audiometric profile by testing each ear at 3 kHz, 4 kHz, and 6 kHz. In this way, a series of six such test sessions could be combined to allow for construction of a partial audiometric profile of the user. By tracking changes to this audiometric profile over time (as additional series of test sessions are run and analyzed), it may be possible to detect changes in the user's hearing threshold that might indicate potential hearing damage. By implementing regular, periodic testing, the hope would be to detect any hearing loss early, in order to have the ability to take steps to reduce noise exposure and prevent or minimize permanent hearing loss. Also, this type of short, informal testing (designed to allow for self-testing to approximate the hearing threshold), while less precise than full audiometric testing, is so convenient that it may be carried out regularly without unduly interfering with a typical work schedule, thus serving as a screening tool to identify candidates of potential hearing loss who may then be directed to more thorough audiometric testing (of the sort carried out by audiology experts in controlled conditions, for example). Full audiometric testing is quite time intensive, so the use of a pre-screening approach may enable more efficient monitoring and testing.

A variety of audiometric test protocols could be implemented by the electronics unit. Typically, for each frequency being tested, the estimated hearing threshold would be determined by iteratively honing-in on the lowest sound pressure level that a user may be likely to hear. A plurality of test sound stimuli would typically be used, with the user's responses (indicating whether the sound stimuli were heard or not) being used to determine the succeeding test sound stimuli sound pressure level.

Figure 9:
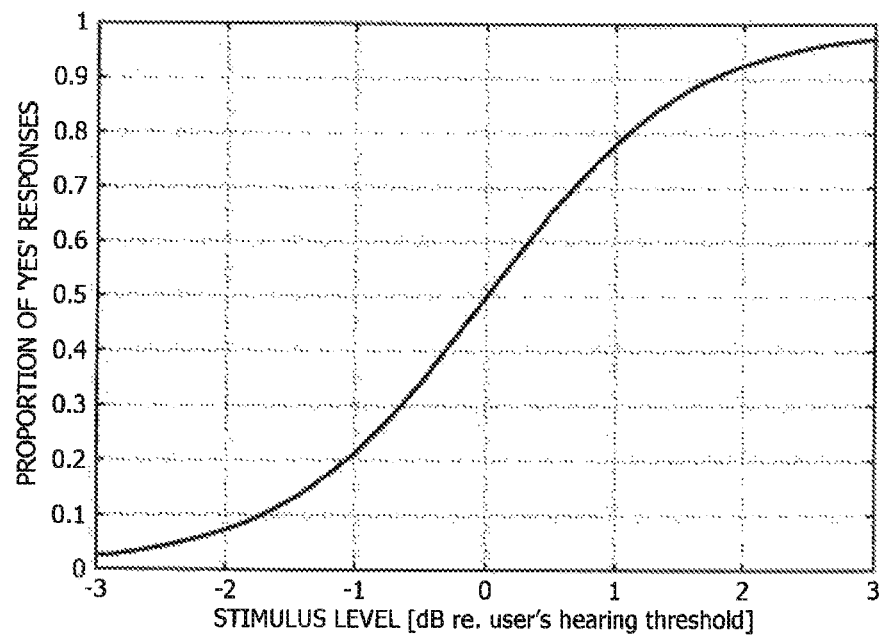
FIG. 9 illustrates an exemplary psychometric function.

In one embodiment, a statistical modeling approach could be used to hone-in on the user's estimated (probable) hearing threshold. The statistical model would typically use the user's responses to determine the succeeding test sound stimulus level and/or to refine the probability that a particular sound pressure level would be the hearing threshold. This technique might employ a type of curve fitting, in which the model determines the user's estimated hearing threshold based on effectively fitting a curve to the user's responses. One example of such a statistical approach might use the psychometric function. So in one embodiment, the user's hearing threshold would be determined using a statistical model like the psychometric function that describes the probability for a positive user response as a function of the stimulus level. The psychometric function defines a curve that has a sigmoid characteristic, shaped such that it approaches 0 for very low stimulus levels and 1 for very high stimulus levels. Thus, the psychometric function might be used to model the probability for a positive user response as a function of the stimulus level. FIG. 9 illustrates an exemplary generic psychometric function curve. It should be understood that the psychometric function is merely one example of an acceptable statistical model that could be used to estimate the probability for a positive (or negative) user response as a function of the stimulus level, and that other mathematical models could alternatively be used.

Figure 10:
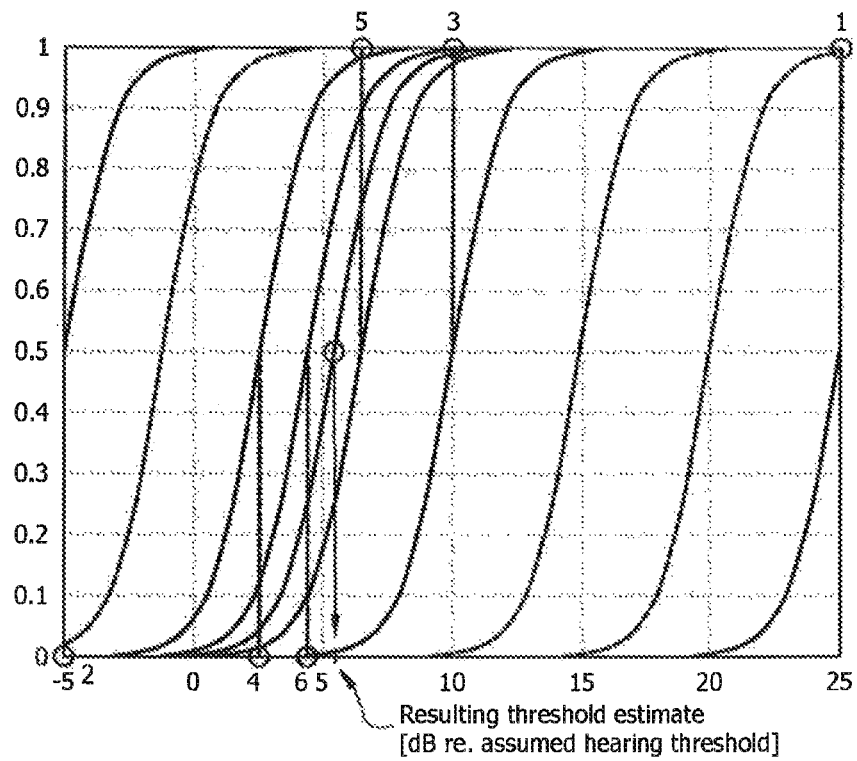
FIG. 10 illustrates several exemplary curves showing translation or displacement of the psychometric function on the x-axis in an exemplary iterative process.

The psychometric function typically is a single mathematical formula that has a parameter that effectively determines the displacement of the curve along the stimulus axis (typically defined as the x-axis). Thus, the psychometric function could be thought of as a series of related curves with varying displacement with respect to the stimulus axis (see for example FIG. 10). The psychometric function models the probability for a positive response at various sound stimulus levels (with the probability approaching zero percent at low sound stimulus levels and the probability approaching one hundred percent at high sound stimulus levels). In relation to this function, the hearing threshold would typically be defined as the stimulus level that corresponds to 50% probability of a positive user response (which typically corresponds to half-way up the probability y-axis). The psychometric function typically has a pre-set shape, but its displacement along the x-axis (the stimulus level axis) may be unknown prior to the audiometric test. The displacement along the x-axis would then typically be determined based on the user's responses during audiometric testing, with user responses being used to update the probability rating for different hypotheses (curve displacements) in order to iteratively hone-in on the most likely hypothesis (and thus the most likely hearing threshold) based on the test data. In one embodiment, displacement along the x-axis may be determined during the test based on the Maximum Likelihood principle, such that after any given number of stimulus-response pairs, the probability that the statistical model could have generated the observed data (stimulus-response pairs) is maximized. Alternatively, a Maximum A Priori principle could be used to find the most probable model given the data. In one embodiment, the next stimulus level would be selected such that it coincides with the present hearing threshold level estimate (which would typically correspond to 50% probability of a positive user response (half-way up the y-axis) for the hypothesis with the highest probability based on current data). For a positive response the next sound stimulus would typically then be below the previous sound stimulus level, and for a negative response the next sound stimulus would typically be above the previous sound stimulus level based on the statistical modeling principles. It is an inherent property of such a statistical method that, with an increasing number of observed stimulus-response pairs, the deviation between succeeding stimulus levels will typically become smaller. The method therefore allows for iterative honing-in on the hearing threshold with added precision.

In one embodiment, the initial sound stimulus might be set at a fairly high sound pressure level (which might be a pre-set number, or might be based on the user's assumed hearing threshold based on pre-existing information) in order to get the user's attention (although optionally, the initial sound stimulus could be set at any sound pressure level, and could proceed upward from a low sound pressure level, for example). The iterative series of tests (i.e. sound stimuli) would typically proceed until a stop condition occurs. In an embodiment, the stop condition may be a pre-set number of iterations (typically between 5 and 10). In another embodiment, the stop condition could be a difference between succeeding stimulus levels that is sufficiently small (such as less than 2 dB). In an embodiment, each test session would test only a single ear for a single frequency, and the electronics unit would cycle through a series of test sessions (each with a different frequency and/or ear) in order to test the entire range of the audiometric profile according to the test protocol. In other words, the profile would be generated by compiling the series of test sessions, and then the series might start again (to begin gathering data for the next profile in time).

Figure 7:
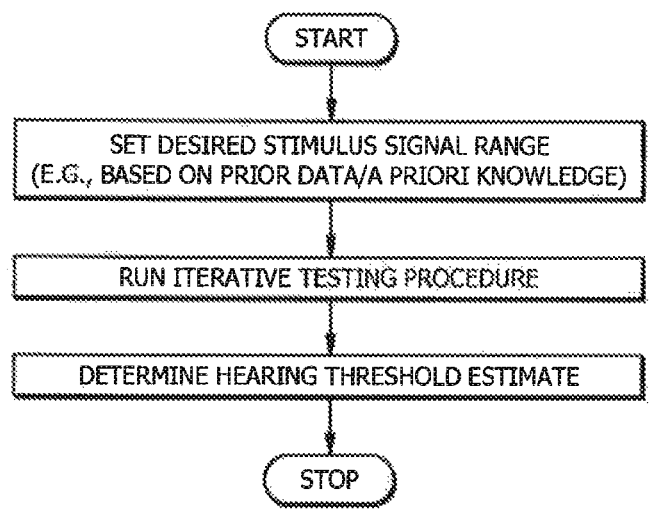
FIG. 7 is a diagram of an embodiment of an audiometric testing protocol using the psychometric function.
Figure 8:
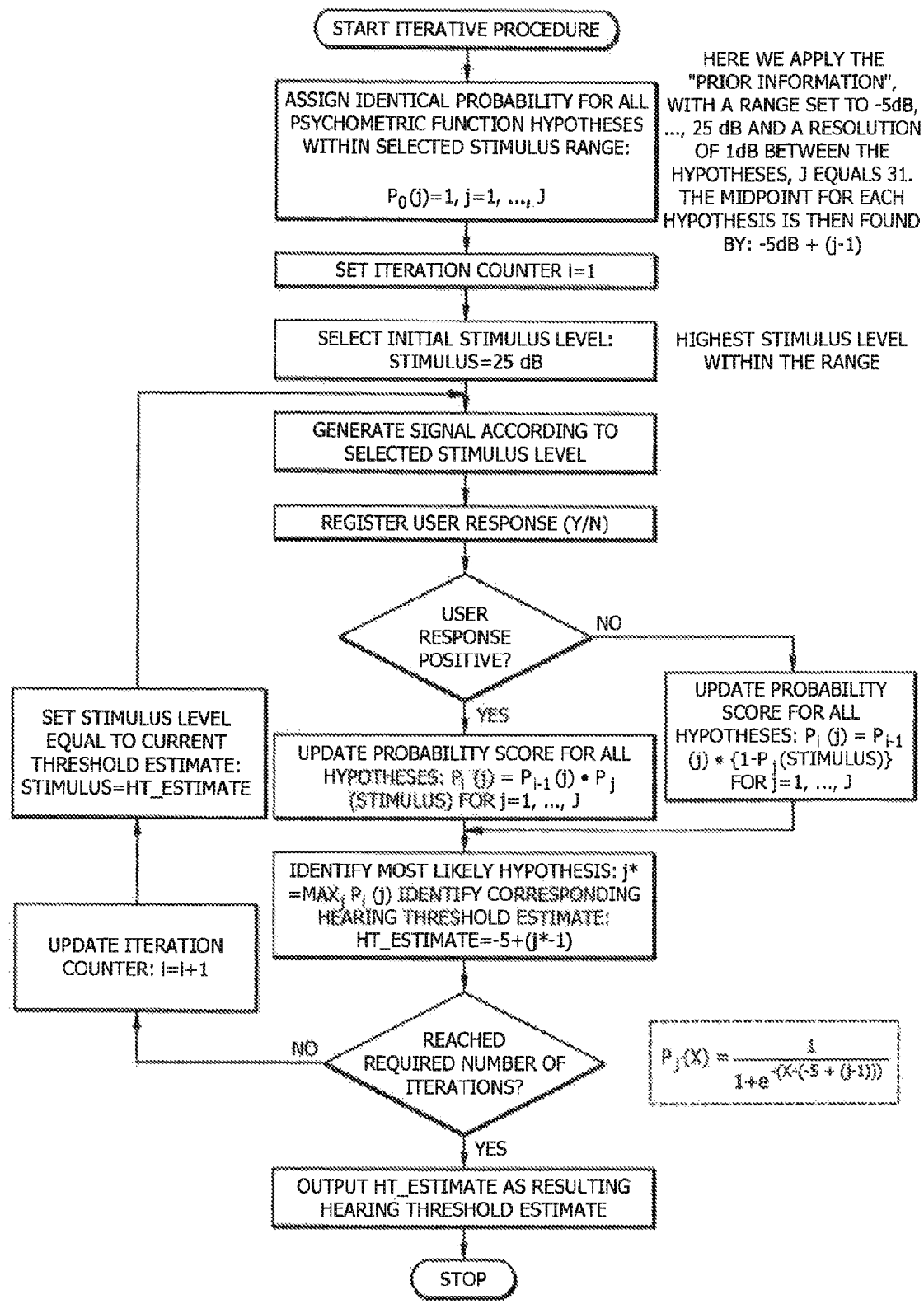
FIG. 8 is a diagram of an embodiment of an iterative test process for determining the estimated hearing threshold using the psychometric function.

The following example of such a process using the psychometric function may be helpful in understanding how it may generate an estimated hearing threshold. FIG. 7 illustrates an exemplary maximum a priori approach, while FIG. 8 illustrates an exemplary iterative process for determining the user's estimated hearing threshold using the psychometric function. This exemplary model uses prior information to initialize the probabilities of the various hypotheses in the psychometric function, with a window of −5 dB to +25 dB and a resolution of 1 dB between hypotheses. The hypotheses within the window (i.e. from −5 dB below the level provided by the prior information to +25 dB above the a priori level) are all initialized to the same level or score, with an identical probability score being set for all psychometric function hypotheses in the selected window. While these hypotheses could be set to any positive number, typically they would be initialized to 1. The initial sound stimulus level would typically be set at the top end of the window (i.e. +25 dB above the a priori level), in an attempt to get the user's attention. The signal (and corresponding sound stimulus transmitted into the user's ear) would be generated at the selected level, and then the user would either register a positive response or not (which could be characterized as a negative response) depending on whether the user hears the sound stimulus and activates the interface (within a reasonable pre-defined timeframe), for example. Based on the user's response, the probability score for each hypothesis would be updated. Typically, for a positive response the probability score would be updated by multiplying the previous probability score for a hypothesis by the value of the psychometric function; for a negative response, on the other hand, the probability score for a hypothesis would be updated by multiplying the previous probability score for a hypothesis by one minus the value of the psychometric function. This updated probability would be calculated for each hypothesis. The psychometric function (with a resolution of 1 dB between each hypothesis) in this example might be defined as follows:

$$p_j(x) = \frac{1}{1 + e^{-(x-(-5+(j-1)))}}.$$

In such an exemplary formula, x represents the sound stimulus sound pressure level (in dB relative to the threshold value assumed by the prior information) of the test signal and j represents the specific hypothesis (curve) in the series of displaced curve hypotheses (with j counting from 1, which corresponds to the hypothesis coinciding with a threshold 5 dB below that assumed by the prior information, to 31, which corresponds to hypothesis coinciding with 25 dB above that assumed by the prior information). The most likely hypothesis would then be the one that has the highest updated probability score, and the estimated hearing threshold would then be the location on the x-axis corresponding to 50% on the y-axis for this most likely hypothesis (which in this example might be defined as −5+(j*−1), in which j* represents the specific hypothesis with the highest probability score). If the stop condition (which might be a specific number of iterations, such as 6 for example) has been reached, then the current estimated hearing threshold would become the final estimate of the user's hearing threshold. If the stop condition has not yet been met, then the test sound stimulus level would be set to the current estimate of the hearing threshold, and the process would continue iteratively until the stop condition is met (and a final estimated hearing threshold is determined). In this way, a statistical approach using the psychometric function could determine an estimated hearing threshold based on user responses to sound stimuli during an audiometric test for a specific frequency level. This approach could be used at different frequency levels in different ears to develop an audiometric profile that might be used to detect possible damage.

So in one embodiment, any prior information on the user's hearing threshold for the frequency being tested (such as the results of the previous test) could be used to set an assumed threshold that may help fix the testing parameters. For example, A 30 dB sound pressure test window of [−5 25] could be used, to set the test parameters about the a priori assumed threshold. If there is no such prior information, then the assumed threshold could be set arbitrarily, and might for example be set based on a standard level for non-impaired humans (which might, for example be based on a minimum audibility curve typically used for calibrating a full audiometric test, perhaps using 10 dB Hearing Level (dBHL) as the assumed threshold). By iteratively testing at sound pressure increments based on the window parameters, the test procedure may hone-in on the actual threshold (by varying the sound pressure level of the test based on the test protocol and the user's responses to determine an estimate of the actual threshold).

Whenever the user hears a sound stimulus, the user will indicate detection by activating the user interface within a reasonable timeframe after generation of the sound stimulus by the speaker, thereby registering a positive "yes" response/reply (indicating that the user heard the sound stimulus at that sound pressure level). On the other hand, if the user fails to activate the user interface within a reasonable timeframe after generation of the sound stimulus by the speaker, then this registers as a negative "no" response/reply (indicating that the user did not hear the sound stimulus at that sound pressure level). And in this embodiment, six iterations might typically be used, since this typically results in a good level of accuracy in a short period of time. It is also possible to set upper and lower limits for the test sound stimulus. For example, the upper limit for sound stimulus might typically be limited to a safe level that would not be likely to cause any hearing damage (such as about 85-90 dB, for example). And a lower limit might be set to ensure that the test operates in a range that is useful for detecting normal levels of hearing (i.e. the test does not need to detect abnormally sensitive threshold levels, below 5 dB for example).

It should also be noted that the timeframe for a positive response is typically set based on the standard reaction time of a typical user. Typically, the timeframe should be no less than approximately one second (to allow for adequate reaction time), and should be no more than approximately 5 seconds (to ensure that the test session is kept short and that the user will not be as tempted to register false positive results). More typically, a timeframe of approximately 1-3 seconds would be used in the embodiment, with approximately 1.5 seconds being preferred from the start of the stimulus signal (which typically is about 0.5 seconds duration). One concern in administering such tests is that users might fall into a pattern of responses (which could lead to false positives, for example) if the timeframe between test signals is too uniform. To address this concern, it might be possible in one embodiment to randomize the length of times between sound stimuli signals. Thus, the quiet time between sound stimuli during a test session (which would typically be greater than or equal to the timeframe for response) could be randomized to intervals between about 1 and about 5 seconds, with about 2-3 seconds being more typical. In one embodiment, the pause/quiet time preceding a stimulus sound could be randomized only in the instance when the previous stimulus resulted in a positive user response, while in the instance that the user did not respond to the previous stimulus the pause would typically be kept at a standardized minimum (typically 1.5-2 seconds)

In other words, in some embodiments the pause (quiet time) between stimuli would be randomized following positive responses, but would be a set, standardized amount following negative responses (with the standardized amount following negative responses typically being kept to a minimum duration to shorten the test as much as reasonably possible). And typically, the randomized pause following a positive user response might be equal to or greater than the standardized minimum (such that after a positive user response, the pause might effectively be a randomized amount, typically between about 0-3 seconds, in addition to the standardized minimum). This would contribute to break any user response patterns, while the test session would still be kept as short as possible. In one embodiment the standardized minimum pause would be kept at about 2 seconds when the previous stimulus resulted in a negative user response, and a randomized pause between about 2 and about 5 seconds in duration would only be used in instances when the previous stimulus resulted in a positive user response.

Figure 13:
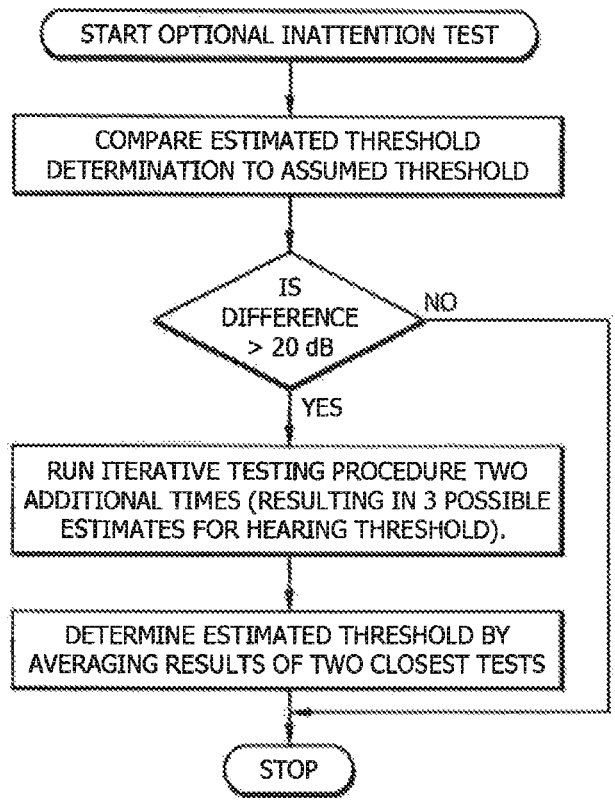
FIG. 13 is a diagram of an embodiment of a procedure for detecting inattention and correcting the estimated hearing threshold.

Another concern is the possibility that the user might fail to respond to a particular sound stimulus, even though they can hear the sound stimulus, due to inattention. This type of error might lead to an estimated hearing threshold that is significantly above the actual threshold. To correct such possible errors, it might be advisable to repeat the test in an attempt to achieve a more accurate result if too high a threshold is detected. So for example, the criteria for retest might be if the estimated hearing threshold is determined to be more than about 15-20 dB from the assumed threshold. In such instances, then the test could be re-run two additional times (on the assumption that the user would be unlikely to be inattentive over multiple tests), with the closest two test results being averaged to determine the ultimate estimated hearing threshold. FIG. 13 illustrates an embodiment of an exemplary procedure for detecting and addressing possible inattention.

Alternatively, non-statistical approaches could be used to estimate the user's hearing threshold. In such embodiments, traditional approaches like staircase methods (up-down methods) or Bekesy's tracking method could be used. A staircase method generally uses a series of descending and ascending trial runs, with turning points (or reversals) whenever a descending run transitions to an ascending run, or vice versa. With the simple '1-down-1-up' method, the stimulus level is increased for every negative response and decreased for every positive response. The increment step size is typically kept fixed for a run (either up or down). The test may end when a pre-set number of turning points (typically six to eight) has been reached. The first reversal may be discarded, with the threshold then typically being calculated as the mean of the midpoints of the remaining runs. In some embodiments, better results may be achieved with 2-down-1-up or 3-down-1-up approaches, in which case the step sizes in the descending runs are larger than the step sizes in ascending runs (typically doubled or tripled, respectively). In Bekesy's tracking method, the level of the stimulus is automatically varied at a fixed rate (with a continuous signal of varying intensity in which the direction of intensity change may be controlled by the user's interaction with the user interface), typically of about ±2 dB per second. The subject is asked to press a button when the stimulus is detectable. Once the button is pressed, the stimulus level automatically decreases (at the fixed rate) until the button is released, at which time the stimulus level increases (at the fixed rate, so long as the button is not pushed) until the button is once again pressed by the user. So in the Bekesy method, the user effectively controls the direction of change to the intensity level of the sound stimulus signal, while also signaling positive and negative responses (regarding whether they hear the signal at a particular intensity level) that may provide information about their hearing threshold. Typically several up and down runs are also used in the Bekesy method, and stop criteria and threshold calculations can be done in a similar manner as for the staircase methods. Both the staircase and Bekesy methods result in a zig-zag approach for iteratively honing-in on the hearing threshold. The following is an exemplary staircase audiometric testing protocol for reference. For each frequency being tested in this staircase method embodiment, the hearing threshold for a user's ear would be determined by honing-in on the lowest sound pressure level that a user can hear (or alternatively, for example, by honing in on the highest dB level that the user cannot hear). So for example, the test might begin with a high sound pressure level (which might be set sufficiently high so that it will be easy for even those with some hearing damage to detect, but preferably not so high that it could be damaging) for the initial test frequency.

By way of example, the test of such an embodiment (employing a 2-down-1-up staircase method) could start at approximately 60 dB (with the electronics unit signaling the speaker to generate a sound stimulus of 60 dB for the frequency being tested). Alternatively, the starting point could be a pre-set amount, for example, 30 dB, above the most recent test results (so that it factors in a priori information in an attempt to increase accuracy/speed). Whenever the user hears a sound stimulus, the user will indicate detection by activating the user interface (and if the user does not activate the user interface within a reasonable timeframe, then that would register as a negative response). After the user indicates that the sound stimulus has been heard, the sound pressure level of the sound stimulus would then be reduced periodically until the user no longer detects the sound stimulus (which is indicated by the failure of the user to activate the user interface within the pre-set timeframe following the generation of the sound stimulus by the speaker). Then the sound pressure level of the sound stimulus may be increased periodically (typically with a smaller step size) until the user once again detects the sound stimulus (as indicated by the user once again activating the user interface in the timeframe following sound stimulus). This up and down process may continue until the desired number of turning points has been achieved. In this way, the user's hearing threshold for the tested ear for the tested frequency could be determined (by incrementally honing-in on the actual threshold using a staircase method).

So for example, in such an embodiment the audiometric testing apparatus might begin with an initial sound stimulus (at the designated test frequency) of 60 dB, and then periodically lower the sound pressure level of the next sound stimulus by 10 dB (such that each succeeding sound stimulus is approximately 10 dB lower than the preceding sound stimulus). In this instance, the succeeding sound stimulus will be lowered (as discussed above) so long as the user indicates detection within an appropriate timeframe (typically less than approximately 5 seconds) following the tested sound stimulus. This series of reducing sound pressure levels continues until the user does not indicate detection within the appropriate timeframe (which registers as a negative response, indicating that the user did not hear the sound stimulus). The audiometric testing apparatus may then periodically increase the sound pressure level of the sound stimulus by 5 dB over the preceding (undetected) sound stimulus level, until the user indicates detection (by activating the user interface within the appropriate time frame). This up and down process would typically be repeated (with several runs) until the desired number of turning points is achieved. Then, the estimated threshold could be determined based on averaging the midpoints of several runs. In this way, the embodiment of the audiometric testing apparatus may determine the user's hearing threshold at the tested frequency in the tested ear. This entire process could be repeated (optionally over one or more test sessions) for each ear at each frequency of the audiometric test regimen, in order to generate an audiometric profile for the user.

Figure 11:
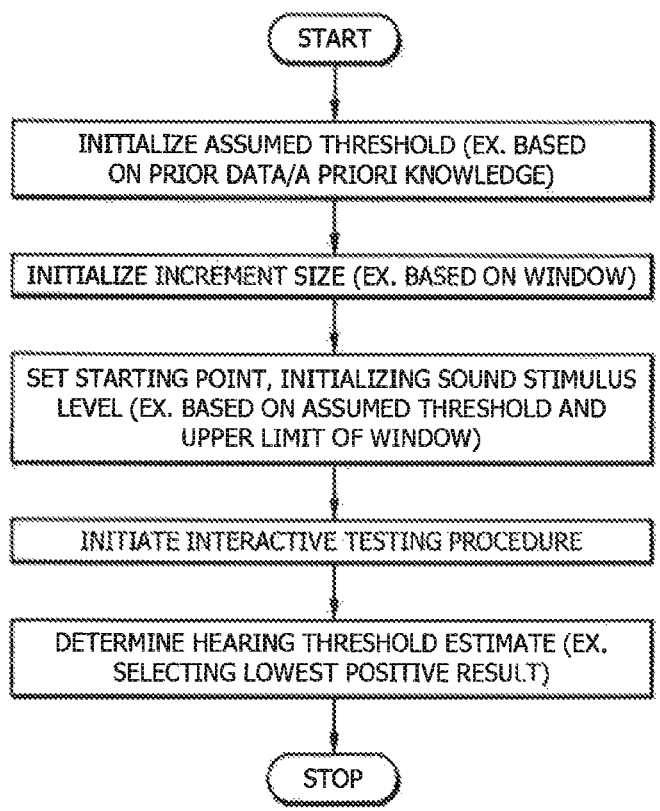
FIG. 11 is a diagram of an embodiment of a non-statistical iterative audiometric testing protocol.
Figure 12:
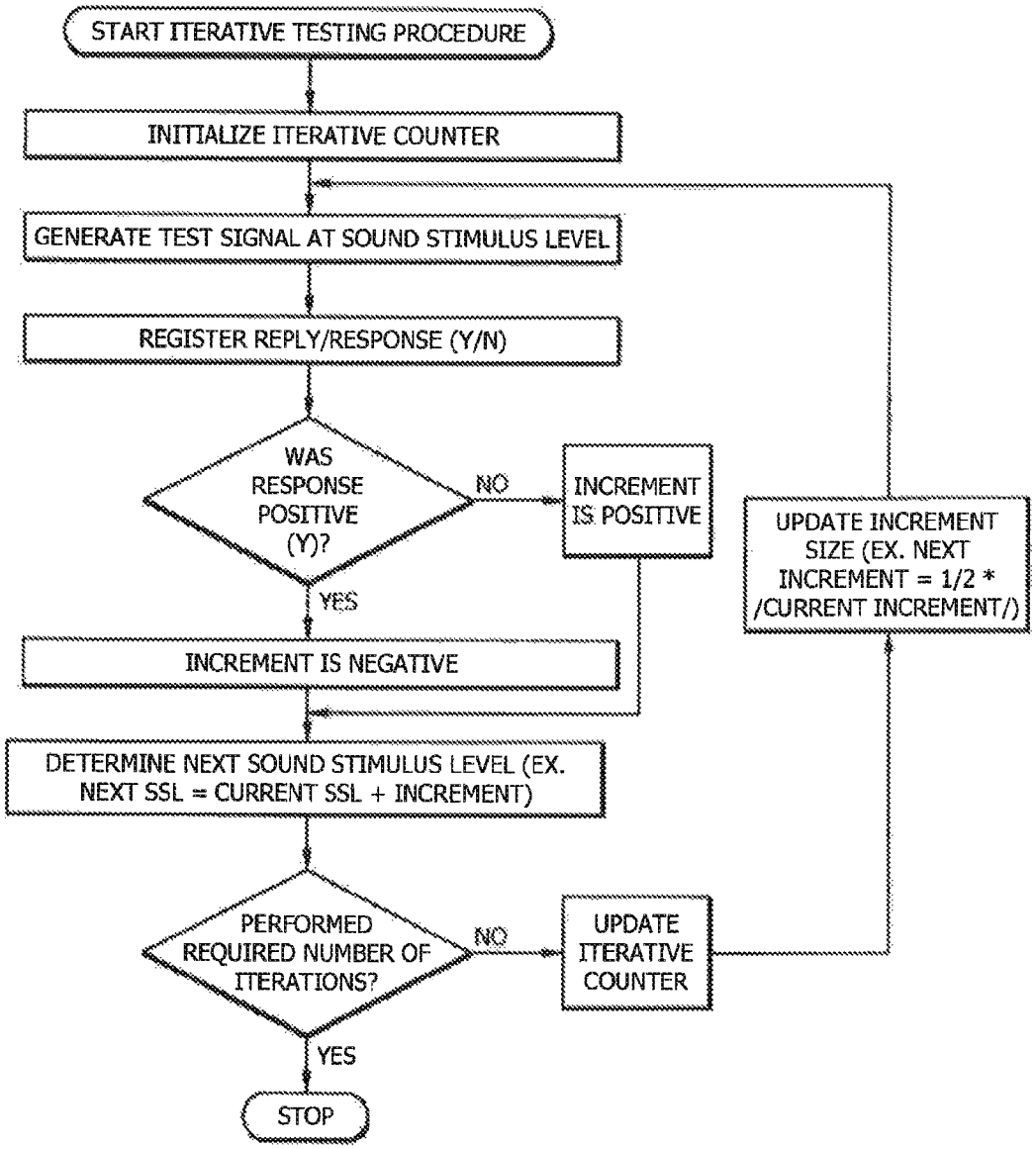
FIG. 12 is a diagram of an embodiment of an iterative test process using shrinking increments.

Alternative shrinking increment audiometric testing procedures (such as an iterative method in which the increment between sound stimuli becomes smaller over time to provide a more refined way to incrementally hone-in on the hearing threshold) are also possible. For example, a fairly large increment could initially be used, with increments then becoming smaller as the process continues, to provide increased granularity (and in one embodiment of such a shrinking increment method, each increment might be half of the previous increment). Typically, for each positive response the next sound stimulus might be set at a level that is an increment below the previous sound stimulus level, and for each negative response the next sound stimulus might be set at an increment above the previous sound stimulus level. The stop condition for such a method might then be a pre-defined number of iterations (typically between five to ten), a pre-set number of up and down runs, or a sufficiently small increment between sound stimuli (with the estimated hearing threshold then being determined by averaging the midpoint of runs or based on the lowest positive result, for example). FIG. 11 illustrates broadly an embodiment of such a shrinking increment audiometric testing process, with FIG. 12 providing more details regarding such an iterative testing procedure for this embodiment. Regardless of the specific iterative testing method used in a specific embodiment, the starting point, size of increments, changes to increment size, number of iterations and/or stopping criteria for honing-in on the user's hearing threshold can be varied depending on specific testing needs. While the embodiments described above may be preferred as a blend of speed and accuracy, it should be understood that many alternative embodiments are possible and are intended to be included within the scope of this disclosure.

Regardless of the testing procedure/protocol, the audiometric testing apparatus might for example be programmed to develop a partial user audiometric profile by testing only at 3, 4, and 6 kHz. This testing would usually be performed over a series of test sessions, however, and each test session would only partially test the pre-set range. So in this specific example, only one ear will be tested for only one of the designated test frequencies making up the partial user audiometric profile each test session (and so it will take 6 test sessions to compile the entire partial user audiometric profile). The first test session of this example might then test the right ear at 3 kHz. The next (second) test session, the user might be tested at 3 kHz in the other ear, and then the user might be tested at the next (third) session at 4 kHz for the right ear, and then at 4 kHz for the left ear in the next (fourth) session, and then at 6 kHz in the right ear in the next (fifth) session, and finally 6 kHz in the left ear in the next (sixth) session. That way, after 6 test sessions, an entire user (partial) profile would be generated. Typically then, the testing series might restart with the next session (at 3 kHz for the right ear). By collecting this test data regarding the user's hearing threshold (and audiometric profile) over time, it may be possible to detect hearing damage by comparing test results over time.

The test protocol regarding which frequency to test in which ear for each session and/or the specific series of sound stimuli to generate for a test session would typically be stored in the electronics unit of the audiometric testing apparatus. Alternatively, the test protocol could be stored in an external storage medium that may be accessed and read by the electronics unit, or it could even be stored on an outside computer, with the electronics unit communicating with the computer for direction. And the results of the test (i.e. the user's hearing threshold) may be stored within the electronics unit, stored on external storage media, or transmitted to a separate computer that may store and analyze the data. In an embodiment, the electronics unit stores the test results for one or more sessions, with this information then transmitted periodically or occasionally to a computer for storage and possible analysis.

In an embodiment, the electronics unit might include an interface for uploading the test results to a separate computer system. The interface could be either wired or wireless. By way of example, a wireless interface with a limited range might be used, such that the user could upload the information to the computer system by passing the electronics unit in proximity to a reader/sensor associated with the computer system. If the sensor is located near an exit (such as a gate) from the work area, this might allow uploading automatically as the user exits the work area while the user is wearing the device. Alternatively, the user could be required to place the electronics unit in close proximity to the sensor (for example, swiping the electronics unit over the sensor). In another embodiment, the data could be transferred at greater distance, using cell wireless technology for example.

In yet another embodiment, the electronics unit could be plugged directly into a base unit that is connected to the computer system, allowing for uploading through a direct physical connection. If this approach is used, the base unit might be configured with slots for each electronics unit assigned to personnel in the work area. Then, each worker could house their electronics unit in the appropriate slot during their off time (when they are not in the work area that requires hearing protection), allowing for uploading of data overnight, for example. In such an embodiment, the electronics unit might optionally also be recharged while plugged in. In another embodiment, the electronics unit could have removable storage media (such as a data card or memory stick, for example). The removable storage media could either serve as the sole memory storage for the test results in the electronics unit, or the electronics unit could have internal memory storage that is permanently affixed, along with a port that allows for download and or copying of the information from this internal memory storage to an external removable storage media device (such as a data card or memory stick). Regardless, in an embodiment with removable memory storage media, the test data could be uploaded by removing the removable storage media (once the data has been transferred to it) and plugging it into a port or reader/scanner associated with the external computer system.

Once the data has been uploaded to the external computer, it may be analyzed over time to screen for possible early detection of temporary hearing loss (although in other embodiments, this analysis could be performed by the electronics unit itself). Typically, such a screening would be accomplished by comparing the current test results to earlier test results, looking for significant change or shift in the hearing threshold or a hearing threshold that is above a certain, pre-defined level (pre-determined to represent likely hearing damage or risk of damage). This screening could be performed initially by the computer in an automated fashion, in order to flag any users and/or entries of concern for further review by expert personnel. Alternatively, the results could be transmitted for review directly by expert personnel for analysis. Typically, if an initial determination of concern is made based on the estimated hearing threshold test results from the current device, then more thorough follow-up audiometric tests might be performed on the user (typically a full assessment by an audiologist, for example).

While any type of sound stimulus might be used during testing (so long as it represents approximately the required frequency and sound pressure level), more typically the sound stimulus would be pure tone. Alternatively, the sound stimulus could be a chirp. A chirp sound stimulus may be easier to detect in the presence of background noise, which would allow for more effective testing within the workplace environment. In an embodiment, the chirp might last approximately 100 to 500 milliseconds, varying in frequency slightly over that interval. So for example, a chirp for testing the frequency of 3 kHz might actually vary between approximately 2.7 and approximately 3.4 kHz over the designated time interval (although any range of frequency values at or near the target frequency could be used to achieve an approximation of the actual target frequency). And in one embodiment, the chirp would vary frequency towards the higher frequency (starting near the low end of the range and ending near the high end of the range). Alternatively, the frequency variation could change (for example, varying first upward towards the higher end of the frequency range and then varying downward towards the lower end of the range). The pattern of frequency variation for a chirp has many possible variants, all of which are intended to be included within the scope of this disclosure.

Embodiments of the device might typically comprise a sealing section (for preventing noise from reaching the user's eardrum), such as a hearing protection device; a loudspeaker or other sound generator for producing the sound stimuli for the audiometric tests; and an electronics unit for generating the test signal that is fed to the loudspeaker (which might be configured or programmed with the test protocol, and/or which might include memory storage that contains the test protocol) and comprising a user interface for controlling the test (such as activating the test procedure, by way of example) and/or receiving/registering user responses (such that when the user activates the user interface, the electronics unit is able to determine if it is a positive or negative response, with a signal being sent to the memory), a memory for storing responses and/or test results, and optionally an interface for uploading the test results to an external computer system. In more advanced models designed to allow for measurement of actual noise exposure at the user's eardrum (by incorporating inward facing microphone elements that may be useful in determining if the background noise penetration is too high for an effective test, if the user has been exposed to potentially damaging noise levels that might warrant an immediate and/or more thorough test, and/or to verify the validity of the stimulus signal, by way of non-exclusive example), embodiments of the device might also include a microphone for monitoring sound incident upon the eardrum (i.e. underneath the hearing protection device) and signaling the electronics unit, and the electronics unit might further comprise memory for storing exposure data (from the microphone) while also being configured to assess noise exposure based on the signal from the microphone. If the electronics unit determines that the inner microphone detects a possibly damaging noise level, it may automatically administer a hearing test session. The electronics unit could optionally analyze the noise exposure data to determine the specific frequency (or frequencies) of most concern, and then administer a test session related to one or more of these frequencies. Similarly, such devices could be configured to check for sound leakage (i.e. leakage control) due to improperly installed hearing protection by, for example, generating an acoustic measurement signal using the loudspeaker, detecting the signal picked up by the internal microphone, and comparing the signal being picked up to stored results corresponding to a good seal. Or alternatively, such devices could be configured to use the internal microphone to verify the validity of the stimulus signal generated by the speaker (by comparing the detected signal to a standard for frequency and/or volume) to ensure that the loudspeaker is operating correctly. Doing so might allow for measurement and/or control of the stimulus signal level parameter and/or the stimulus signal-to-noise and distortion ratio.

Advanced models of the device might also include an outer microphone for detecting external sounds, which might allow for feed-through of external sounds at safe (filtered) levels to improve communication during a work shift (by allowing some verbal communication despite the use of hearing protection). For example, this might provide a talk-through feature, allowing the user to communicate more freely while still being protected from potentially damaging external noise levels. Typically, this type of feed-through/talk-through feature would be deactivated or overridden during audiometric testing (since it could interfere with the accuracy of the testing in determining the hearing threshold). Such devices could also be configured for optional active noise reduction (for example, in addition to passive noise reduction provided by the sealing section/hearing protection device), by using the outer microphone to detect external sounds and/or the inner microphone to detect sound at the eardrum, processing the detected sound to provide a signal for active noise cancellation, and using the loudspeaker to generate the acoustic cancellation signal. And advanced models of the device might also include a communication assembly (capable of receiving and/or transmitting communication signals, such as wireless signals) that transmits incoming communication and/or entertainment signals to the loudspeaker for playback within the user's ear (under the hearing protection). Again, this communication/entertainment feature would typically be deactivated/overridden during audiometric testing. U.S. Pat. Nos. 6,567,524; 6,661,901; 7,039,195; and 6,754,359 (owned by the assignee of the present application) may provide some additional details regarding possible additional features, and they are hereby incorporated by reference to the degree that they are not inconsistent with the information specifically set forth herein. All of such advanced model features are intended to be optional, and any or all such features might be included (or excluded) from any specific device, perhaps along with other optional features.

Turning now to specific embodiments of the device, FIG. 1 illustrates a cross-section of a hearing protection device, along with an exemplary audiometric testing apparatus. In the embodiment shown in FIG. 1, the hearing protection device may be a cylindrical or bullet-shaped foam earplug 20. The earplug 20 in FIG. 1 has a sound generator 22, such as a speaker, mounted in the proximal (inner) tip (i.e. the end designed to be inserted into the user's ear canal and to be closest to the user's ear drum). The embodiment of FIG. 1 also has an electronics unit 24 located external to the hearing protection device. Typically, the electronics unit 24 would be worn clipped or attached to the user's clothing, or it could be worn from a lanyard. In the embodiment of FIG. 1, the external electronics unit 24 would be in electrical communication with the speaker 22, so that the electronics unit may supply signals to the sound generator 22. In FIG. 1, the electronics unit 24 is electrically coupled to the speaker by a cable 25, a jack or terminal 26, and a wire 27. The wire 27 runs the length of the earplug 20 and connects the speaker 22 to the jack 26, allowing the speaker to receive external electrical signals even while the earplug 20 is inserted into the user's ear. The jack 26 is an optional feature that allows for connection of a removable cable or wire 25 to the internal wire 27 within the earplug (leading to the speaker). If no jack 26 is used, then the wire 27 would extend out to connect to the external electronics unit directly (i.e. the cable and the wire would be integrated). This electronic coupling allows the electronics unit 24 to transmit electrical signals to the speaker, directing/causing the speaker 22 to generate sound stimulus at one or more frequencies in order to implement an audiometric test.

In the embodiment shown in FIG. 1, the housing of the electronics unit also contains the user interface 28, which serves to allow the user to signal during the audiometric test when sound stimulus is detected. In this embodiment, the user interface 28 is a push button, although any sort of electrical communication device could alternatively be used (for example a microphone for voice activation based on speech/audio recognition or a touch sensitive screen could be alternatives). And some variants of the embodiment of FIG. 1 also optionally include a dosimeter function, having a microphone located in the proximal (inner) tip of the earplug 20 near the speaker 22 that can detect the sound level within a user's ear canal when the earplug is in place for analysis by the electronics unit (which in its dosimeter role also determines if a dangerous level of sound impinges on the user's ear). If a dangerous level of sound is penetrating the hearing protection device, then the electronics unit may signal the user via an optional visual warning device 29, indicating that the user may wish to take protective steps, remove themselves from the noise environment, and/or run an audiometric test to see if there has been any hearing loss. Alternatively, the electronics unit might automatically administer an audiometric test (which might focus on detected frequencies of concern). Or if the background level of noise is too high for effective audiometric testing, the electronics unit might signal the user (and perhaps prevent initiation of a test session). Alternatively, the user could be warned of the dangerous noise levels using the speaker.

In practice, the embodiment of FIG. 1 typically employs a pair of hearing protection devices attached to the electronics unit, to provide hearing protection for both ears. The user inserts the earplugs 20 into both ears to seal the ear canal (providing passive hearing protection). The user would generally wear the earplugs for some duration greater than the length of the test, typically wearing them for substantially the entire duration of exposure to a noise environment (such as throughout a shift). Typically, the earplugs are foam, and typically the material provides passive sound attenuation to protect the user from potentially damaging noise environments. Examples of foam that might be used are polyurethane or polyvinyl chloride. Alternatively, personal moulds could be used. So for example, the earplugs might provide protection in a range from about 15 to 35 dB NRR, and more preferably might provide hearing protection of about 28 NRR or more. When the user wishes to initiate an audiometric test, the electronics unit would transmit one or more signals to the sound generator (while the earplugs are still inserted in the user's ear canal), running the audiometric test. In response to the signal(s) from the electronics unit, the sound generator would generate one or more sound stimulus, creating a sound field in the user's meatus to implement the audiometric test. If the user is able to hear the sound stimulus generated by the sound generator, then the user would activate the user interface to register a positive response (thereby signaling the electronics unit that the sound stimulus was detected). If the user is unable to hear the sound stimulus, then the user would not activate the user interface within the designated timeframe, registering as a negative response (indicating that the user was unable to hear the sound stimulus). The electronics unit would record the response (typically on some memory storage medium), and may also use the response to adjust the sound stimulus level based on the feedback from the user. Then the electronics unit might generate another signal to the sound generator to further implement the audiometric test in an iterative fashion. FIG. 4 is similar in function, but employs a different sort of sound sealing element with flanges (allowing for press-in insertion, for example).

FIGS. 2, 3, and 5 are also similar in function, but have the electronics unit integrally formed with the hearing protection device to form an in-ear unit (with the entire device either all or mostly located within the user's ear). These figures employ a sound tube or channel 30 which provides access to the ear canal through part or all of the hearing protection (sound sealing element) so that the speaker may generate the necessary sound stimulus for testing in the ear canal (with FIG. 2 also having an electrical connection 31 (such as a wire) from the speaker to the electronics unit).

Figure 14:
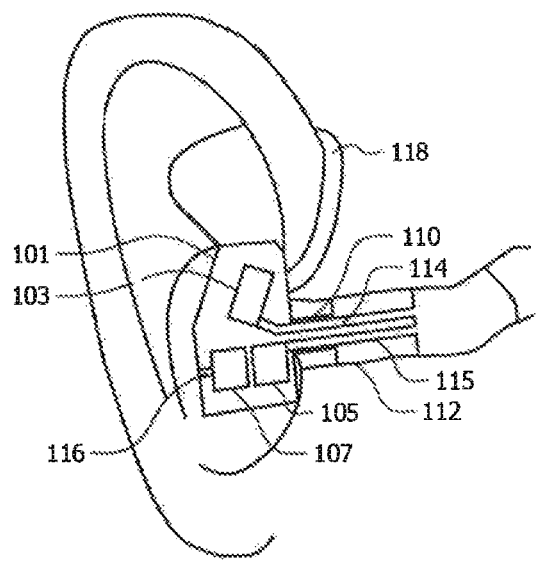
FIG. 14 is a sectional view of an embodiment of an ear-piece with talk-through capabilities.

The embodiment shown in FIG. 14 illustrates an earpiece variant of the device, which may be used with an external electronics unit (while also showing how the earpiece relates to the user's ear when in position). This device comprises an earpiece housing 101, which contains a loudspeaker 103, an inner microphone 105, and an outer microphone 107. Extending from the housing is an insert portion 110, which is designed to be inserted into an ear canal. The insert portion 110 includes a sealing element 112 that forms a secure fit within the user's ear canal to passively block sound infiltration into the user's eardrum, serving as a passive attenuation hearing protection device. Additionally, there is a sound tube 114 that leads from the speaker's face, through the sealing section of the insert portion, and to the ear canal. Sound tube 114 directs the sound stimulus produced by the speaker 103 into the user's ear canal (so that it is incident upon the user's eardrum). Sound tube 115 leads from the inner microphone's face 105, through the sealing section of the insert portion, and to the ear canal. Sound tube 115 allows for the inner microphone 105 to detect noise levels within the user's ear canal (i.e. the sound incident upon the user's eardrum). In other words, the microphone might be directed towards the meatus. Sound tube 116 leads from the outer microphone 107, through the housing 101, to open to the outside world, allowing the outer microphone 107 to detect external noise. It should be understood that sound tubes may not be required in embodiments in which the microphone and/or speaker elements can be mounted directly on the appropriate face of the device.

Wire 118 of FIG. 14 connects the earpiece to an external electronics unit. The external electronics unit would typically include a user interface, storage memory with the audiometric testing protocol/procedures, and storage memory for the user's responses during the test and the test results, and would be configured to run the audiometric test (by for example generating sound stimulus signals to direct the speaker 103 to generate sound stimulus within the user's ear, recording responses, iteratively modifying the sound stimulus level based on user responses, determining the estimated hearing threshold, and remembering which frequency to test for a given test session). Optionally, the electronics unit may also filter the external sound detected by the outer microphone (by filtering the signal to ensure that sounds are only reproduced at a safe level) and direct the speaker 103 to generate the filtered sounds within the user's ear (thereby allowing speak-through capabilities). The electronics unit of this embodiment would automatically deactivate this feature, however, during audiometric testing. Another optional feature of this device might be an assessment of noise exposure. The electronics unit would then be configured to assess noise exposure based on the signal from the inner microphone 105, and store noise exposure data on memory. And the electronics unit might also optionally have an interface for uploading of information from the memory/storage to an external computer system.

Figure 15:
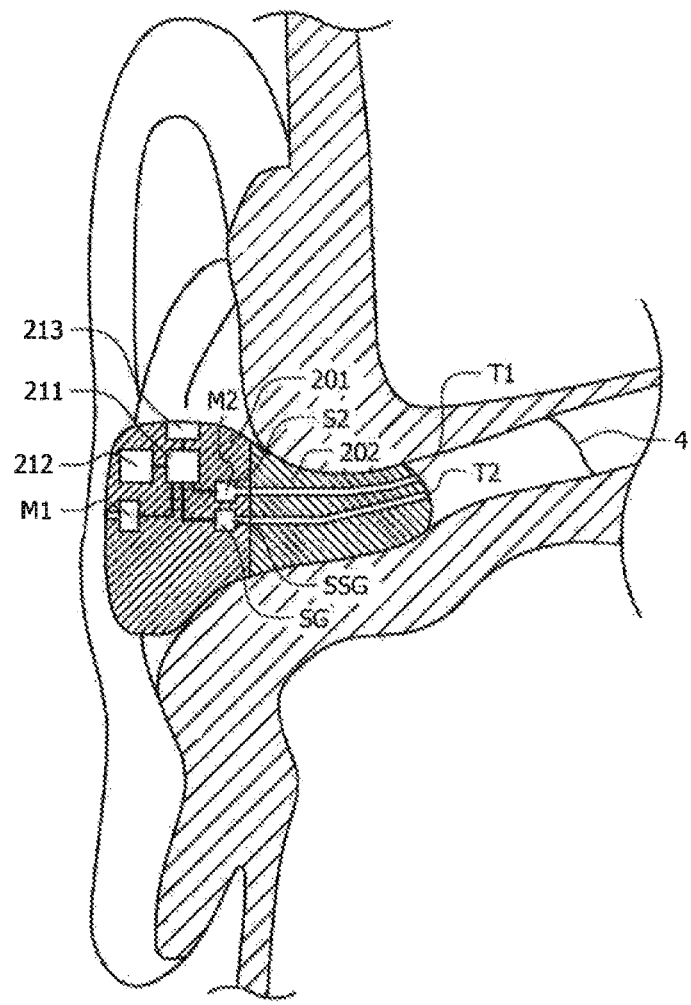
FIG. 15 is a sectional view of an embodiment of an all-in-ear earpiece.

The embodiment of FIG. 15 shows a complete all-in-ear device with capabilities for passive sound attenuation, active sound attenuation, noise exposure monitoring, leakage control, talk-through, and communication/entertainment, featuring passive sealing, electro-acoustic transducers, and electric circuitry. The ear terminal of FIG. 15 comprises an outer section arranged for sitting adjacent to the outward facing portion of the sealing section and a part of the inward facing portion of the outer section is formed to fit the concha around the outer portion of the meatus. External sounds are attenuated by the sealing section (typically in the form of an earplug), inserted into the outer part of the ear canal or meatus. Optionally, external sounds may also be attenuated using active noise control, which is achieved by using one or two microphones M1 (an outer microphone), M2 (an inner microphone) and a loudspeaker SG together with electronic circuits in an electronics unit 211 mounted in the device. Algorithms for active noise control are generally known and thus will not be described in detail herein, but may include active noise cancelling feedback of acoustic signals converted by at least one of the microphones through the loudspeaker SG.

The ear terminal of FIG. 15 comprises a main section 201 containing two microphones M1, M2 and a loudspeaker SG. The main section 201 is designed to provide comfortable and secure placement in the concha. A sealing section 202 is attached to the main section. The sealing section 202 may be an integral part of the ear terminal, or it may be removable/interchangeable. The sound inlet of the outer microphone M1 is connected to the outside of the ear terminal, picking up external sounds. Inner microphone M2 is connected to the inner portion of the meatus by means of an acoustic transmission channel T1. The sound outlet of the loudspeaker SG is open to the inner portion of the meatus by means of another acoustic transmission channel T2 between the loudspeaker SG and the inward facing portion of the sealing section. It should be understood that when smaller microphones and speakers are available, it may be possible to mount inner microphone M2 and speaker SG directly at the innermost part of the sealing section 202, such that there would be no need for transmission channels.

The two microphones and the loudspeaker are connected to an electronics unit 211, which may optionally be connected to other equipment by an interface 213 that may transmit digital and/or analog signals, and also possibly power. The electronics and optionally a power supply 212 (such as a battery) may be included in main section or in a separate section. The main section of the ear terminal may be made of standard polymer materials of the sort that are used for hearing aids, for example. The sealing section may be made of a resilient, slowly re-expanding shape retaining polymer foam like PVC, PUR or other materials suitable for earplugs and other hearing protection devices. The channels may also be made of polymer wall material (or some other non-conforming material) in order to prevent their collapse when the sealing section is inserted into the meatus.

Figure 16:
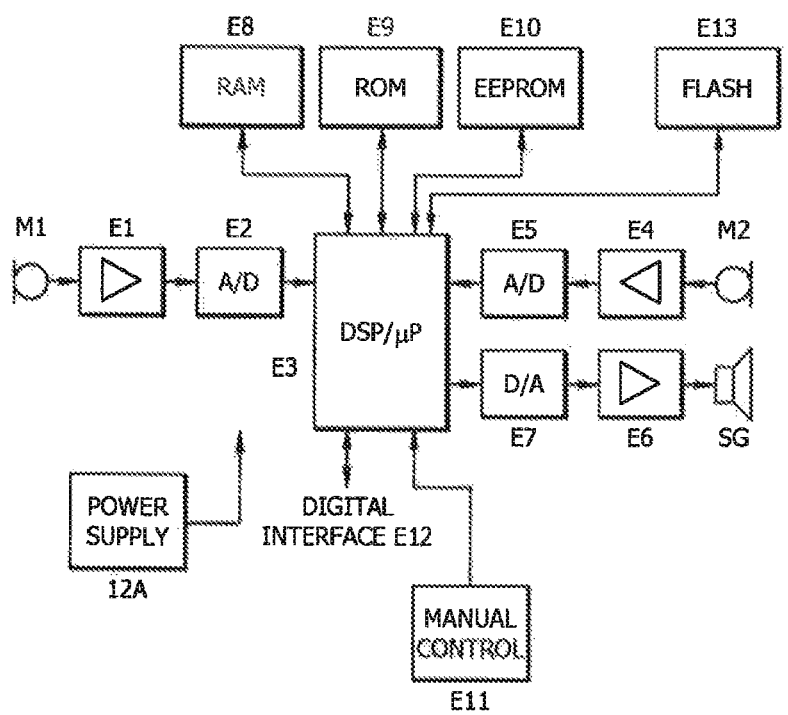
FIG. 16 is a diagram of an embodiment of an electric circuit capable of implementing audiometric testing.

The electronics unit 211 may comprise electric circuitry as shown in FIG. 16, which may be configured and/or programmed to achieve several possible functions. By way of example, in an embodiment the outer microphone M1 may pick up ambient (external) sound. A signal from the outer microphone M1 may be amplified in E1 and sampled and digitized in an analog-to-digital converter E2 and then fed to a processing unit E3 that may be a digital signal processor (DSP), a microprocessor, or a combination of the two. A signal from the inner microphone M2, which picks up sound in the meatus between the sealing section and the eardrum, may be amplified in amplifier E4 and sampled and digitized in the analog-to-digital converter E5 and fed to the processing unit E3. A desired digital signal is generated in the processing unit E3. This signal is converted to analog form in the digital-to-analog converter E7 and fed to the analog output amplifier E6 that drives the loudspeaker SG. The sound signal produced by the loudspeaker SG is fed to the eardrum (tympanum) via channel T2 as described above.

The processing unit E3 in this embodiment is connected to memory elements such as flash memory E13, RAM (random access memory) E8, ROM (read only memory) E9, and EEPROM (electronically erasable programmable read only memory) E10. The memories E8, E9, E10, and E13 are used for storing computer programs, filter coefficients, test responses, test results, noise exposure data, analysis data, and/or other relevant data. The electronic circuitry may be connected to other electrical units via interface E12 (which may be via cable or wireless through a digital radio link, such as Bluetooth standard). A manual control signal may be generated in manual control E11 and fed to the processing unit E3. The control signal may be generated using a user interface with buttons, switches, etc. and may be used to turn the unit on and off, to change operation mode, to signal responses, etc. In an alternative embodiment, a predetermined voice signal may serve as control signal. The electric circuitry is powered by power supply 12A (which may be 212 in FIG. 15) that may be a primary or rechargeable battery arranged in the ear terminal or in a separate unit, or may be an electrical power connection.

Audiometric testing may be attained by using the loudspeaker SG to generate sound stimulus in the meatus according to an audiometric program or protocol. Specifically, upon activation (which may be by the user via the user interface) the processor may access the test protocol from memory storage E10 (along with perhaps the recorded data indicating which portion of the series of tests will be run this session) and direct an initial signal which may be D/A converted, amplified, and fed to the loudspeaker SG. The processor may then receive a response from the user interface (such as manual control E11) and record the response to memory (such as E8). Based on the response, the processor may modify the sound stimulus signal for the next iteration and continue following this iterative process according to the protocol. Once the test session is complete according to the protocol, the processor may analyze the stored response results and generate an estimated hearing threshold, which may then be recorded to memory storage (E10). The processor may also transmit some or all of this data to an external computer via interface E12.

Noise exposure monitoring in this embodiment may be attained by using the inner microphone M2 to detect sound levels in the meatus (even while the ear is already protected). The signal from the inner microphone M2 is amplified, A/D converted, and analyzed in DSP or processing unit E3 (eg. a microprocessor) as described above. The result of the analysis is compared to damage risk criteria (stored in memory), and the user may be warned (visually or audibly) whenever certain limits are exceeded (perhaps with a recommendation for initiation of audiometric testing to assess any damage). The signal and/or analysis may also be stored in memory. Additionally, the processor may compare the analyzed signal to criteria to determine if background noise is too high for effective audiometric testing (and may then warn the user or block testing).

Leakage control in this embodiment (i.e. assessing whether the sealing section is effectively in place and operating to seal the user's ear) may be attained by injecting a pre-set acoustic measurement signal into the meatus using the loudspeaker SG, detecting the signal using the inner microphone M2, and analyzing the signal detected by the inner microphone M2 using the electronics unit 211 (which typically compares the incoming detected signal to a baseline stored in memory to determine if they are sufficiently similar to indicate proper sealing of the ear canal). The baseline is usually determined from previous measurements in a situation with good sealing conditions. This process uses the fact that a sound field locally generated in the cavity near the eardrum is influenced by leakage in the hearing protection (such that the transfer function from the input of the loudspeaker SG to the output of the inner microphone M2 is altered if the hearing protection/sealing section is not properly inserted and working effectively). The user may then be warned (visually or audibly, for example) if leakage is unacceptably high. Additionally, it may be possible to attain other functions/features (such as talk-through, communication/entertainment audio input by way of non-exclusive example, based on the configuration and/or programming of the processor.

The present disclosure concerns a method of (preliminarily) screening for hearing loss in the workplace (without removing hearing protection being worn to protect against noise exposure in the workplace and without unduly interfering with work schedule). Conceptually, the idea is to employ a hearing protection device (for wearing in potentially damaging noise environments) that incorporates audiometric testing. More specifically, the method seeks to encourage frequent self-testing (as opposed to the current model of testing, which uses full audiometric testing in a controlled environment by audiologists, perhaps on a yearly basis), in order to more quickly identify potential hearing loss (as a way of screening to prevent or minimize permanent hearing loss). To be effective, however, the frequent self-tests cannot be too long or they will be inconvenient and intrusive to the work schedule, which would hamper implementation and likely lead to poor follow-through. To that end, the method may attempt to allow for testing without removing hearing protection (typically worn throughout the work shift to protect against exposure to potentially damaging noise levels in the work environment), allowing for convenient self-testing on site without the need to involve outside personnel and/or to take the user out of the work environment to the type of controlled environment typically required for full audiometric testing. Additionally, the tests sessions may be kept short, typically no more than a minute, in order to encourage compliance. To accomplish this, embodiments may utilize a series of partial test sessions. So the hope is that using the disclosed hearing protection device with integrated audiometric testing will lead to improved screening and early identification of potential hearing damage (which may in turn allow for more effective corrective action to be taken).

An embodiment of such a method comprises the steps of: sealing the user's ear canal (for example, by applying a hearing protection device to protect the user from potentially damaging external noise, with the hearing protection device substantially worn for the duration of the exposure to the potentially damaging noise, for example the work shift) while the user is in an environment with potential noise exposure (such that the sealing lasts longer than the duration of the audiometric test session, and typically is substantially as long as the external noise exposure, for example the duration of a shift); activating an audiometric test without removing the hearing protection device (which is typically made possible by using a HPD with integrated audiometric testing, as disclosed above); and determining an estimated hearing threshold based on the audiometric test. As described above, the audiometric test may be a partial test session (testing only a portion of the audiometric profile to be determined according to the test protocol), and a series of partial test sessions may be run (typically with only one session per shift or day) and compiled over time to determine the user's estimated audiometric profile (by combining an entire series of test sessions to cover all frequency levels that are to be tested for the audiometric profile). Typically, the hearing protection device would be worn by the user substantially the entire time the user is in an environment of potential noise exposure, and the user may self-initiate a test session without removing the hearing protection, thereby allowing for testing while on the work site.

Another possible concern is that the audiometric test could lead to erroneous results due to user inattention. If a user misses a sound stimulus (i.e. does not respond within the timeframe) that they should have heard if they were paying full attention, it may skew the results. Thus, the method may also optionally check for signs of inattention. By way of example, inattention may be suspected if the final result of the test (i.e. estimated hearing threshold) is significantly above the assumed hearing threshold (for example, more than 20 or 25 dB above the assumed threshold), or alternatively if the hearing threshold is above a certain pre-set level. If possible inattention is detected, one embodiment might repeat the suspect test session two or more times, then possibly throw out the test result(s) that deviates the most, and average the remaining test results to provide a more accurate estimated threshold.

The noise level may also be measured and/or recorded. Optionally, the noise level may then be used to determine if conditions are appropriate for an audiometric test (i.e. checking to ensure that the background noise level is not too high for effective testing). If noise conditions are too loud, then the user may be warned, or the audiometric test may be disabled. The noise exposure level might also be used to warn the user of a potentially damaging exposure, which might recommend immediate testing to determine the likelihood of damage. Additionally, the quality of the seal provided by the hearing protection device may be checked. This might be accomplished by generating a pre-determined sound stimulus in the user's ear canal (underneath the hearing protection device), measuring the transfer from the input of the loudspeaker SG to the output of the inner microphone M2, and comparing the transfer function to criteria corresponding to an adequate seal. If the seal is inadequate, the user might then be warned.

The audiometric test may comprise generation of a series of sound stimuli, registering/recording user responses, and analyzing the responses to determine an estimated hearing threshold. As described above, the series of sound stimuli may be iteratively adjusted based on the user responses to hone-in on the hearing threshold. It is also possible that the audiometric testing could be performed even in loud environments that are not sufficiently attenuated by the hearing protection device by using additional sound attenuation (such as active noise reduction and/or passive noise reduction earmuffs over the earplug-type hearing protection device). By doubling-up on noise reduction measures, it may be possible to sufficiently reduce the background noise level getting through to the user's ear canal to allow for testing at a noisy site. Again, measurement of the noise exposure level may be useful in determining the effectiveness of noise reduction measures. Alternatively, the user may change locations within the work site (to a location with less background noise) to provide conditions favorable to testing. For example, the user might go to a sound isolating chamber set up on site to initiate the self-test. These techniques could also be used in conjunction, if necessary, with the noise exposure measurement possibly providing guidance.

It may also be useful in some embodiments to pre-test the user's hearing (typically using a detailed audiometric test performed by trained audiologists) to provide a benchmark for analysis of hearing damage. This type of outside information may be used as an assumed hearing threshold (which might be used to determine a starting sound stimulus level for testing based on such a priori information), and might also be used as a point of comparison when evaluating changes to the user's hearing threshold to detect possible hearing damage. Once testing is being performed on an on-going basis, the prior results can serve as such a benchmark and/or assumed hearing threshold for succeeding tests. And as discussed above, it might also be useful in some instances to upload the test results (such as estimated hearing threshold) to an external computer, allowing for analysis of potential hearing loss (by looking for changes to the hearing threshold over time, typically by comparing the current estimated hearing threshold to previous results). Alternatively, the analysis could be performed by the electronics unit. Such analysis might be automated (based on pre-set criteria), or it might be performed by transmitting the data to a specialist for review. If this preliminary screening indicates possible hearing damage, then the user might be warned and/or undergo more thorough audiometric testing. Such methods are designed for protecting a user's hearing during a work shift and performing a quick screening for potential hearing loss without unduly interfering with work using a hearing protection device with integrated audiometric testing. Thus, the use of a hearing protection device with integrated audiometric testing, as described above, may provide many advantages in more quickly detecting potential hearing loss, hopefully at an early enough stage to prevent or minimize permanent hearing loss.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field of Invention," for example, the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive. Reference in the disclosure to inner or outer may be made for purposes of description, with "out" or "outer" typically meaning away from the user's eardrum, and "in" or "inner" typically meaning towards the user's eardrum.

What is claimed is:

1. A method of preliminarily screening for hearing loss of a user in the workplace using a hearing protection device comprising a microphone, a sound generation device, an electronics unit, and a user interface, wherein the microphone is acoustically connected to an ear canal of the user via a first sound channel formed in the hearing protection device, wherein the sound generation device is acoustically connected the ear canal of the user via a second sound channel formed in the hearing protection device, wherein the microphone, the sound generation device, and the user interface are each connected to the electronics unit, the method comprising the steps of:
   sealing, by the hearing protection device, the ear canal of the user by applying a sealing section of the hearing protection device within the ear canal;
   measuring, by the microphone via the first sound channel, a noise level within the ear canal;

determining, by the electronics unit, the noise level is potentially damaging to the user's hearing;

activating, by the electronics unit, an automated audiometric test session without removing the hearing protection device from the ear canal of the user;

wherein the audiometric test session is performed by:
producing, by the sound generation device, a series of sound stimuli into the ear canal of the user via the second sound channel;
registering, via the user interface, user responses for each sound stimuli; and
analyzing, by the hearing protection device, the user responses to determine an estimated hearing threshold of the user.

2. The method of claim 1 wherein the series of sound stimuli are each separated by a pause, and wherein the duration of the pause is a standardized minimum following a negative user response, but the duration of the pause includes a randomized amount between about 0-3 seconds in addition to the standardized minimum following a positive user response.

3. The method of claim 1, wherein the hearing protection device is worn in at least one ear of the user for a period of time substantially greater than the duration of the audiometric test session.

4. The method of claim 3,
where the series of sound stimuli are transmitted to the ear canal at a single frequency and at varying sound pressure levels.

5. The method of claim 4 wherein analyzing user responses uses a statistical model.

6. The method of claim 4 wherein the series of sound stimuli are each separated by a pause; and wherein the duration of the pause is a standardized minimum following a negative user response, and the duration of the pause is a randomized amount at least as long as the standardized minimum following a positive user response.

7. The method of claim 3,
wherein the series of sound stimuli comprises a first sound stimulus transmitted into the ear canal of the user at an initial stimulus level and a second sound stimulus transmitted into the ear canal of the user at a second sound stimulus level;
wherein the user responses comprise a first user's response to the initial sound stimulus level; and
wherein the second sound stimulus level is determined based on the user's response to the initial sound stimulus level.

8. The method of claim 7, further comprising:
updating probability scores for a psychometric function hypotheses.

9. The method of claim 4, wherein the audiometric test session is a partial test session among a series of partial test sessions; the method further comprising:
compiling user responses made to the user interface by the user from the series of partial test sessions over time to create an audiometric profile; wherein the audiometric profile is a partial profile; and wherein the partial profile tests a range of frequencies from about 3-6 kHz.

10. The method of claim 7, wherein each of the sound stimuli has a corresponding duration, and each of the sound stimuli varies in frequency throughout the corresponding duration.

11. The method of claim 1,
wherein the sealing section provides sound attenuation to protect the user's ears from potentially damaging external sounds and is configured to be worn comfortably for a period of time that substantially exceeds a duration of the audiometric test session;
wherein the sound generation device produces the series of sound stimuli at various frequencies and sound pressure levels; and
wherein the electronics unit is configured to generate one or more test signals directed to the sound generation device in order to cause generation of the series of sound stimuli for the audiometric test session.

12. The method of claim 1, wherein the electronics unit implements the audiometric test session as a pattern of partial test sessions that, when collated over time, results in an audiometric profile; and wherein the audiometric profile is a partial profile comprising about 3 kHz, about 4 kHz, and about 6 kHz, wherein a partial profile is constructed for the user by compiling six partial test sessions.

13. The method of claim 12, wherein each partial test session tests only a single ear at a single frequency; and wherein each partial test session comprises between 5 to 10 sound stimuli.

14. The method of claim 12, wherein each partial test session iteratively hones-in on the user's hearing threshold.

15. The method of claim 11, wherein the series of sound stimuli comprise an iterative series of sounds for each frequency being tested at various sound pressure levels.

16. The method of claim 15, wherein analyzing user responses to determine an estimated hearing threshold uses a statistical model; wherein the statistical model comprises the psychometric function; wherein the statistical model estimates the user's hearing threshold; wherein each of the sound stimuli has a corresponding duration, and wherein each of the sound stimuli varies in frequency throughout the corresponding duration.

17. The method of claim 1, further comprising:
warning the user whenever that noise level is too high for audiometric testing.

18. The method of claim 1, wherein the series of sound stimuli are incrementally adjusted based on user responses to the user interface in order to iteratively hone-in on the hearing threshold.

19. The method of claim 1, wherein each sound stimuli is a chirp varying in frequency throughout a duration of the chirp.

20. The method of claim 1, wherein the hearing protection device further comprises a second microphone connected to the electronics unit and acoustically connected externally of an ear of the user via a third sound channel formed in the hearing protection device, the method further comprising:
detecting, by the second microphone, sounds external to the ear of the user;
processing, by the electronics unit, the sounds to provide a signal for active noise cancellation; and
generating, by the sound generation device, an acoustic cancellation of the sounds external to the ear of the user.

* * * * *

UNITED STATES PATENT AND TRADEMARK OFFICE
CERTIFICATE OF CORRECTION

PATENT NO.       : 9,895,088 B2
APPLICATION NO.  : 15/263907
DATED            : February 20, 2018
INVENTOR(S)      : Viggo Henriksen et al.

Page 1 of 1

It is certified that error appears in the above-identified patent and that said Letters Patent is hereby corrected as shown below:

On the Title Page

Page (2), OTHER PUBLICATIONS, Line 3: delete the extra spaces between "Abstract," and "http"

In the Claims

Column 26, Line 58: insert --to-- after the word "connected"

Signed and Sealed this
Fourteenth Day of August, 2018

Andrei Iancu
*Director of the United States Patent and Trademark Office*